US012599706B2

(12) United States Patent
Appel et al.

(10) Patent No.: US 12,599,706 B2
(45) Date of Patent: *Apr. 14, 2026

(54) ADHESION PREVENTION WITH SHEAR-THINNING POLYMERIC HYDROGELS

(71) Applicant: The Board of Trustees of the Leland Stanford Junior University, Stanford, CA (US)

(72) Inventors: Eric Andrew Appel, Stanford, CA (US); Y. Joseph Woo, Stanford, CA (US); Lyndsay Stapleton, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 9 days.

This patent is subject to a terminal disclaimer.

(21) Appl. No.: 18/608,675

(22) Filed: Mar. 18, 2024

(65) Prior Publication Data

US 2024/0299632 A1     Sep. 12, 2024

Related U.S. Application Data

(63) Continuation of application No. 16/590,189, filed on Oct. 1, 2019, now Pat. No. 11,975,123, which is a continuation-in-part of application No. 15/943,358, filed on Apr. 2, 2018, now Pat. No. 11,969,526.

(60) Provisional application No. 62/739,550, filed on Oct. 1, 2018, provisional application No. 62/480,636, filed on Apr. 3, 2017.

(51) Int. Cl.
| | |
|---|---|
| *A61L 31/04* | (2006.01) |
| *A61L 31/14* | (2006.01) |
| *C08L 1/08* | (2006.01) |
| *C08L 67/02* | (2006.01) |

(52) U.S. Cl.
CPC .......... *A61L 31/041* (2013.01); *A61L 31/042* (2013.01); *A61L 31/145* (2013.01); *A61L 31/148* (2013.01); *C08L 1/08* (2013.01); *C08L 67/025* (2013.01); *A61L 2300/424* (2013.01); *A61L 2400/06* (2013.01); *C08L 2203/02* (2013.01); *C08L 2205/22* (2013.01)

(58) Field of Classification Search
None
See application file for complete search history.

(56) References Cited

U.S. PATENT DOCUMENTS

| | | | |
|---|---|---|---|
| 4,192,727 A | 3/1980 | Ward | |
| 5,143,724 A | 9/1992 | Leshchiner et al. | |
| 5,410,016 A | 4/1995 | Hubbell et al. | |
| 5,480,436 A | 1/1996 | Bakker et al. | |
| 5,785,993 A | 7/1998 | Baker et al. | |
| 5,888,988 A | 3/1999 | Elson | |
| 6,150,581 A | 11/2000 | Jiang et al. | |
| 6,673,093 B1 | 1/2004 | Sawhney | |
| 6,818,018 B1 | 11/2004 | Sawhney | |
| 7,125,860 B1 | 10/2006 | Renier et al. | |
| 7,347,850 B2 | 3/2008 | Sawhney | |
| 8,455,001 B2 | 6/2013 | Ito et al. | |
| 8,709,450 B2 | 4/2014 | Kaneko et al. | |
| 8,728,524 B2 | 5/2014 | Bellini et al. | |
| 8,748,409 B2 | 6/2014 | Kaneko et al. | |
| 8,778,326 B2 | 7/2014 | Lu et al. | |
| 8,859,523 B2 | 10/2014 | Prestwich et al. | |
| 8,916,143 B2 | 12/2014 | Putnam et al. | |
| 9,089,730 B2 | 7/2015 | Shalev et al. | |
| 9,289,279 B2 | 3/2016 | Wilson et al. | |
| 11,969,526 B2 * | 4/2024 | Appel | A61L 31/06 |
| 11,975,123 B2 * | 5/2024 | Appel | A61L 31/042 |
| 2002/0042473 A1 | 4/2002 | Trollsas et al. | |
| 2003/0180251 A1 | 9/2003 | Friedrich et al. | |
| 2004/0023842 A1 | 2/2004 | Pathak et al. | |
| 2005/0271727 A1 | 12/2005 | Yao | |
| 2006/0177481 A1 | 8/2006 | Sawhney | |
| 2007/0001156 A1 | 1/2007 | Toreki | |
| 2008/0069857 A1 | 3/2008 | Yeo et al. | |
| 2008/0107703 A1 | 5/2008 | Tabata et al. | |
| 2009/0294049 A1 | 12/2009 | Udipi et al. | |
| 2010/0285113 A1 | 11/2010 | Shoichet et al. | |
| 2010/0291055 A1 | 11/2010 | Athanasiadis et al. | |
| 2011/0178184 A1 | 7/2011 | Kaneko et al. | |
| 2012/0298777 A1 | 11/2012 | Holladay et al. | |
| 2015/0202299 A1 | 7/2015 | Burdick et al. | |

(Continued)

FOREIGN PATENT DOCUMENTS

| | | |
|---|---|---|
| EP | 2511336 A1 | 10/2012 |
| KR | 20060011503 A | 2/2006 |

(Continued)

OTHER PUBLICATIONS

U.S. Appl. No. 15/943,358, Advisory Action mailed on Jun. 14, 2023, 3 pages.
U.S. Appl. No. 15/943,358, Final Office Action mailed on Feb. 19, 2021, 17 pages.
U.S. Appl. No. 15/943,358, Final Office Action mailed on Mar. 17, 2023, 9 pages.
U.S. Appl. No. 15/943,358, Non-Final Office Action mailed on Sep. 11, 2023, 11 pages.
U.S. Appl. No. 15/943,358, Non-Final Office Action mailed on Aug. 6, 2020, 12 pages.
U.S. Appl. No. 15/943,358, Non-Final Office Action mailed on Jul. 29, 2022, 8 pages.

(Continued)

*Primary Examiner* — Melissa S Mercier
(74) *Attorney, Agent, or Firm* — Kilpatrick Townsend & Stockton LLP

(57)     ABSTRACT

A method of preventing tissue adhesion includes forming an incision in tissue, applying a hydrogel to tissue through the incision, and closing the incision with the hydrogel therein. The hydrogel includes a polymer non-covalently cross-linked with a plurality of nanoparticles and prevents a formation of adhesions between tissues and/or organs.

20 Claims, 29 Drawing Sheets

(56)                    References Cited

U.S. PATENT DOCUMENTS

| | | | |
|---|---|---|---|
| 2016/0030789 A1 | 2/2016 | Cordani | |
| 2016/0228601 A1 | 8/2016 | He et al. | |
| 2016/0287745 A1 | 10/2016 | Grinstaff et al. | |
| 2017/0196818 A1 | 7/2017 | Shin et al. | |
| 2017/0319506 A1 | 11/2017 | Appel et al. | |
| 2017/0362380 A1 | 12/2017 | Christman et al. | |
| 2018/0086896 A1 | 3/2018 | Appel | |
| 2018/0280586 A1 | 10/2018 | Appel et al. | |

FOREIGN PATENT DOCUMENTS

| | | | | |
|---|---|---|---|---|
| KR | 20170110882 A | 10/2017 | | |
| WO | 9317669 A1 | 9/1993 | | |
| WO | 03084481 A2 | 10/2003 | | |
| WO | 2005110377 A1 | 11/2005 | | |
| WO | 2013076305 A1 | 5/2013 | | |
| WO | 2013124654 A1 | 8/2013 | | |
| WO | 2014116187 A1 | 7/2014 | | |
| WO | 2014125418 A1 | 8/2014 | | |
| WO | 2015172073 A1 | 11/2015 | | |
| WO | WO-2016049360 A1 * | 3/2016 | ............. | A61K 47/30 |

OTHER PUBLICATIONS

U.S. Appl. No. 15/943,358, Notice of Allowance mailed on Dec. 20, 2023, 8 pages.

U.S. Appl. No. 16/590,189, Final Office Action mailed on Jun. 28, 2023, 13 pages.

U.S. Appl. No. 16/590,189, Non-Final Office Action mailed on Jan. 26, 2023, 11 pages.

U.S. Appl. No. 16/590,189, Non-Final Office Action mailed on Sep. 8, 2023, 13 pages.

U.S. Appl. No. 16/590,189, Notice of Allowance mailed on mailed on Jan. 24, 2024, 9 pages.

U.S. Appl. No. 16/590,189, Notice of Imported Citations mailed on Jan. 31, 2024, 4 pages.

U.S. Appl. No. 16/590,189, U.S. Patent Application No., Adhesion Prevention With Shear-Thinning Polymeric Hydrogels, Oct. 1, 2019, 75 pages.

U.S. Appl. No. 16/709,832, U.S Patent Application No., Biomimetic, Moldable, Self-Assembled Cellulose Silica-Based Trimeric Hydrogels and Their Use as Viscosity Modifying Carriers in Industrial Applications, Dec. 10, 2019, 64 pages.

U.S. Appl. No. 17/281,014, U.S Patent Application No., Injectable Hydrogels for Controlled Release of Immunomodulatory Compounds, Mar. 29, 2021, 52 pages.

Adusumilli et al., Regional Delivery of Mesothelin-targeted Car-T-Cell Therapy Generates Potent and Long Lasting Cd4-dependent Tumor Immunity, Science Translational Medicine, vol. 6, No. 261, 2014, 31 pages.

Appel et al., Activation Energies Control the Macroscopic Properties of Physically Cross-linked Materials, Angewandte Chemie International Edition, vol. 53, No. 38, Sep. 15, 2014, pp. 10038-10043.

Appel et al., Exploiting Electrostatic Interactions in Polymer-Nanoparticle Hydrogels, American Chemical Society Macro Letters, vol. 4, No. 8, Aug. 18, 2015, pp. 848-852.

Appel et al., Formation of Single-chain Polymer Nanoparticles in Water Through Host-guest Interactions, Angewandte Chemie International Edition vol. 51, No. 17, Apr. 23, 2012, pp. 4185-4189.

Appel et al., Gluing Gels: A Nanoparticle Solution, Nature Materials, vol. 13, No. 3, Mar. 2014, pp. 231-232.

Appel et al., Self-Assembled Hydrogels Utilizing Polymer-Nanoparticle Interactions, Nature Communications, vol. 6, No. 6295, Feb. 19, 2015, pp. 1-9.

Appel et al., Supramolecular Cross-Linked Networks via Host-Guest Complexation with Cucurbit[8]uril, Journal of the American Chemical Society, vol. 132, No. 40, Oct. 13, 2010, pp. 14251-14260.

Appel et al., Supramolecular Polymeric Hydrogels, Chemical Society Reviews, vol. 41, No. 18, Aug. 2012, pp. 6195-6214.

Appel et al., Sustained Release of Proteins from High Water Content Supramolecular Polymer Hydrogels, Biomaterials, vol. 33, No. 18, Jun. 1, 2012, pp. 4646-4652.

Appel et al., The Control of Cargo Release from Physically Cross-linked Hydrogels by Crosslink Dynamics, Biomaterials, vol. 35, No. 37, Dec. 1, 2014, pp. 9897-9903.

Appel et al., Ultrahigh-Water-Content Supramolecular Hydrogels Exhibiting Multistimuli Responsiveness, Journal of the American Chemical Society, vol. 134, No. 28, Jul. 18, 2012, pp. 11767-11773.

Bang et al., Injectable Pullulan Hydrogel for the Prevention of Postoperative Tissue Adhesion, International Journal of Biological Macromolecules, vol. 87, Jun. 2016, pp. 155-162.

Bao et al., Swelling Behaviors of Organic/Inorganic Composites based on Various Cellulose Derivatives and Inorganic Particles, Carbohydrate Polymers, vol. 88, No. 2, Apr. 2012, pp. 589-595.

Bourges et al., Synthesis and General Properties of Silated-Hydroxypropyl Methylcellulose in Prospect of Biomedical Use, Advances in Colloid and Interface Science, vol. 99, No. 3, Dec. 2, 2002, pp. 215-228.

Bremer et al., Laboratory Scale Clean-In-Place (CIP) Studies on the Effectiveness of Different Caustic and Acid Wash Steps on the Removal of Dairy Biofilms, International Journal of Food Microbiology, vol. 106, No. 3, Feb. 15, 2006, pp. 254-262.

Chen et al., Injectable Thermosensitive Hydrogel Containing Hyaluronic Acid and Chitosan as a Barrier for Prevention of Postoperative Peritoneal Adhesion, Carbohydrate Polymers, vol. 173, Oct. 1, 2017, pp. 721-731.

Cheung et al., Scaffolds That Mimic Antigen-presenting Cells Enable Ex Vivo Expansion of Primary T Cells, Nature Biotechnology, vol. 36, No. 2, 2018, pp. 160-169.

Conlon et al., Redistribution, Hyperproliferation, Activation of Natural Killer Cells and CD8 T Cells, and Cytokine Production During First-in-Human Clinical Trail of Recombinant Human Interleukin-15 in Patients with Cancer, Journal of Clinical Oncology, vol. 33, No. 1, Jan. 2015, pp. 74-82.

Drevelle et al., Thermal and Fire Behaviour of Ammonium Polyphosphate/Acrylic Coated Cotton/PESFR Fabric, Polymer Degradation and Stability, vol. 88, No. 1, Apr. 1, 2005, pp. 130-137.

Ehrbar et al., Drug-Sensing Hydrogels for the Inducible Release of Biopharmaceuticals, Nature Materials, vol. 7, No. 10, Oct. 2008, pp. 800-804.

Evans et al., Investigation into the Transportation and Melting of Thick Ice Slurries in Pipes, International Journal of Refrigeration, vol. 31, No. 1, Jan. 1, 2008, pp. 145-151.

Fu et al., Biodegradable and Thermosensitive Monomethoxy Poly(Ethylene Glycol)-Poly(Lactic Acid) Hydrogel as a Barrier for Prevention of Post-Operative Abdominal Adhesion, Journal of Biomedical Nanotechnology, vol. 10, No. 3, Mar. 2014, pp. 427-435.

Gesan-Guiziou et al., Nanofiltration for the Recovery of Caustic Cleaning-in-Place Solutions: Robustness Towards Large Variations of Composition, Journal of Dairy Research, vol. 69, No. 4, Nov. 2002, pp. 633-643.

Gimenez et al., Long-term Forest Fire Retardants: A Review of Quality, Effectiveness, Application and Environmental Considerations, International Journal of Wildland Fire, vol. 13, No. 1, Apr. 27, 2004, pp. 1-15.

Grosskopf et al., Injectable Supramolecular Polymer-nanoparticle Hydrogels Enhance Human Mesenchhymal Stem Cell Delivery, Bioengineering & Translational Medicine, vol. e10147, Oct. 2019, 11 pages.

Gu et al., Study on Preparation and Fire-Retardant Mechanism Analysis of Intumescent Flame-Retardant Coatings, Surface and Coatings Technology, vol. 201, No. 18, Jun. 25, 2007, pp. 7835-7841.

Hales et al., Ice Fraction Measurement of Ice Slurries Through Electromagnetic Attenuation, International Journal of Refrigeration, vol. 47, Nov. 1, 2014, pp. 98-104.

Hall et al., Engineered Luciferase Reporter from a Deep Sea Shrimp Utilizing a Novel Imidazopyrazinone Substrate; ACS Chemical Bilogy, American Chemical Society Chemical Bilogy, vol. 7, No. 11, Nov. 2012, pp. 1848-1857.

(56) References Cited

OTHER PUBLICATIONS

Harada et al., Macroscopic Self-assembly through Molecular Recognition, Nature Chemistry, vol. 3, No. 1, Jan. 2011, pp. 34-37.

Hernandez et al., A Quantitative Description for Designing the Extrudability of Shear-thinning Physical Hydrogels, Macromolecular Bioscience, vol. 21, No. 2, Feb. 2021, 10 pages.

Hoare et al., Prevention of Peritoneal Adhesions Using Polymeric Rheological Blends, Acta Biomaterialia, vol. 10, No. 3, Mar. 2014, pp. 1187-1193.

Hu et al., Detection of Poly-and Perfluoroalkyl Substances (PFASs) in U.S. Drinking Water Linked to Industrial Sites, Military Fire Training Areas, and Wastewater Treatment Plants, Environmental Science & Technology Letters, vol. 3, No. 10, Aug. 9, 2016, pp. 344-350.

Hughes et al., Transfer of a TCR Gene Derived from a Patient with a Marked Antitumor Response Conveys Highly Active T-cell Effector Functions, Human Gene Therapy, vol. 16, No. 4, 2005, pp. 457-472.

Ishiyama et al., The Prevention of Peritendinous Adhesions by a Phospholipid Polymer Hydrogel Formed in Situ by Spontaneous Intermolecular Interactions, Biomaterials, vol. 31, No. 14, May 2010, pp. 4009-4016.

Kapsabelis et al., Adsorption of Ethyl(hydroxyethyl)Cellulose onto Silica Particles: The Role of Surface Chemistry and Temperature, Journal of Colloid and Interface Science, vol. 228, No. 2, Aug. 15, 2000, pp. 297-305.

Karacam et al., Prevention of Pleural Adhesions Using a Membrane Containing Polyethylene Glycol in Rats, International Journal of Medical Sciences, vol. 8, No. 5, 2011, pp. 380-386.

Krielen et al., In-Hospital Costs of an Admission for Adhesive Small Bowel Obstruction, World Journal of Emergency Surgery, vol. 11, No. 49, Oct. 6, 2016, pp. 1-8.

Krishna et al., Protein-and Peptide-modified Synthetic Polymeric Biomaterials, Peptide Science: Original Research on Biomolecules, vol. 94, No. 1, Jan. 20, 2010, pp. 32-48.

Labanieh et al., Programming Car-T-Cells to Kill Cancer, Nature Biomedical Engineering, vol. 2, No. 6, 2018, pp. 377-391.

Liu et al., Reduced Postoperative Intra-Abdominal Adhesions Using Carbylan-SX, a Semisynthetic Glycosaminoglycan Hydrogel, Fertility and Sterility, vol. 87, No. 4, Apr. 2007, pp. 940-948.

Long et al., 4-1BB Costimulation Ameliorates T Cell Exhaustion Induced by Tonic Signaling of Chimeric Antigen Receptors; Nature Medicine, Nature Medicine, vol. 21, No. 6, Jun. 2015, pp. 581-590.

Lotze et al., Clinical Effects and Toxicity of Interleukin-2 in Patients with Cancer, Cancer, vol. 58, No. 12, Dec. 1986, pp. 2764-2772.

Lu et al., Injectable Shear-Thinning Hydrogels Engineered with a Self-Assembling Dock-and-Lock Mechanism, Biomaterials, vol. 33, No. 7, Mar. 2012, pp. 2145-2153.

Maupin et al., Estimated Use of Water in the United States in 2010, US Geological Survey, Circular 1405, 2014, 64 pages.

Merin et al., Cleaning-in-place in the Dairy Industry: Criteria for Reuse of Caustic (NaOH) Solutions, Le Lait, vol. 82, No. 3, May 1, 2002, pp. 357-366.

Miller et al., A First-in-human Phase 1 Study of Subcutaneous Outpatient Human 1L15 (rh1L15) in Adult with Advanced Solid Tumors, Clinical Cancer Research, vol. 24, No. 7, Apr. 2018, pp. 1525-1535.

Moody et al., Monitoring Perfluorinated Surfactants in Biota and Surface Water Samples Following an Accidental Release of Fire-Fighting Foam into Etobicoke Creek, Environmental Science & Technology, vol. 36, No. 4, Feb. 15, 2002, pp. 545-551.

Moody et al., Occurrence and Persistence of Perfluorooctanesulfonate and other Perfluorinated Surfactants in Groundwater at a Fire-training Area at Wurtsmith Air Force Base, Journal of Environmental Monitoring, vol. 5, No. 2, Mar. 10, 2003, pp. 341-345.

Moody et al., Perfluorinated Surfactants and the Environmental Implications of Their Use in Fire-fighting Foams, Environment Science and Technology, vol. 34, No. 18, Sep. 15, 2000, pp. 3864-3870.

Mulyasasmita et al., Molecular-Level Engineering of Protein Physical Hydrogels for Predictive Sol-Gel Phase Behavior, Biomacromolecules. vol. 12, No. 10, Sep. 2, 2011, pp. 3406-3411.

Nakahata et al., Redox-Responsive Self-Healing Materials Formed from Host-Guest Polymers, Nature Communications, vol. 2, No. 511, Oct. 25, 2011, pp. 1-6.

Okabayashi et al., Adhesions After Abdominal Surgery: A Systematic Review of the Incidence, Distribution and Severity, Surgery Today, vol. 44, No. 3, Mar. 2014, pp. 405-420.

Osada et al., The Effect of Cross-Linked Hyaluronate Hydrogel on the Reduction of Post-Surgical Adhesion Reformation in Rabbits, Journal of International Medical Research, vol. 27, No. 5, Sep.-Oct. 1999, pp. 233-241.

Parisi-Amon et al., Protein-Engineered Injectable Hydrogel to Improve Retention of Transplanted Adipose-Derived Stem Cells, Advanced Healthcare Materials, vol. 2, No. 3, Mar. 2013, pp. 428-432.

Park et al., In Situ Supramolecular Assembly and Modular Modification of Hyaluronic Acid Hydrogels for 3D Cellular Engineering, American Chemical Society Nano, vol. 6, No. 4, Apr. 24, 2012, pp. 2960-2968.

Patterson et al., In Situ Characterization of the Degradation of PLGA Microspheres in Hyaluronic Acid Hydrogels by Optical Coherence Tomography, Institute of Electrical and Electronics Engineers Transactions on Medical Imaging, vol. 28, No. 1, Jan. 2009, pp. 74-81.

Petka et al., Reversible Hydrogels from Self-Assembling Artificial Proteins, Science, vol. 281, No. 5375, Jul. 17, 1998, pp. 389-392.

Prestwich, Engineering a Clinically-Useful Matrix for Cell Therapy, Organogenesis, vol. 4, No. 1, 2008, pp. 42-47.

Pritchard et al., An Injectable Thiol-Acrylate Poly(Ethylene Glycol) Hydrogel for Sustained Release of Methylprednisolone Sodium Succinate, Biomaterials, vol. 32, No. 2, Jan. 2011, pp. 587-597.

Quarini et al., Ice-pigging to Reduce and Remove Fouling and to Achieve Clean-in-place, Applied Thermal Engineering, vol. 22, No. 7, May 2002, pp. 747-753.

Quarini et al., Investigation and Development of an Innovative Pigging Technique for the Water-Supply Industry, Proceedings of the Institution of Mechanical Engineers Part E Journal of Process Mechanical Engineering, vol. 224, No. 2, May 1, 2010, pp. 79-89.

Richards et al., Cancer Immunotherapy Gets Assist from Microscale Engineering, Available Online at: https://www.fredhutch.org/en/news/center-news/2019/12/stephan-thin-film-stent-immunotherapy.html, 2021, 7 pages.

Ring et al., Mechanistic and Structural Insight into the Functional Dichotomy between Interleukin-2 and Interleukin-15, Nature Immunology, vol. 13, No. 12, Dec. 2012, pp. 1187-1195.

Rodell et al., Rational Design of Network Properties in Guest-Host Assembled and Shear-Thinning Hyaluronic Acid Hydrogels, Biomacromolecules, vol. 14, No. 11, Nov. 11, 2013, pp. 1-20.

Rodell et al., Shear-Thinning Supramolecular Hydrogels with Secondary Autonomous Covalent Crosslinking to Modulate Viscoelastic Properties in Vivo, Advanced Functional Materials, vol. 25, No. 4, Jan. 28, 2015, pp. 636-644.

Rose et al., Nanoparticle Solutions as Adhesives for Gels and Biological Tissues, Nature, vol. 505, No. 7483, Jan. 16, 2014, pp. 382-385.

Rowland et al., Dynamically Crosslinked Materials via Recognition of Amino Acids by Cucurbit [8] uril, Journal of Materials Chemistry B, vol. 1, No. 23, Apr. 2013, pp. 2904-2910.

Salem et al., Porous Polymer and Cell Composites That Self-Assemble in Situ, Advanced Materials, vol. 15, No. 3, Feb. 5, 2003, pp. 210-213.

Schroeder, Can Fire Suppressant Gels Protect Log Decks. A Case Study to Test the Concept, Wildland Fire Operations Research Group, 2005, 7 pages.

Schroeder, Can Fire Suppressant Gels Protect Log Decks? Part III—Two Case Studies to Test Gel Effectiveness Against Radiant and Convective Heat Transfer, Dave Schroeder, FERIC, Nov. 2006, 8 pages.

Schroeder, Effectiveness of Forest Fuel Management: A Crown Fire Case Study in the Northwest Territories, Canada, Forest Engineering Research Institution of Canada, Nov. 2006, 7 pages.

(56)　　　　　References Cited

OTHER PUBLICATIONS

Shaner et al., A Bright Monomeric Green Fluorescent Protein Derived from Branchiostoma Lanceolatum, Nature Methods, vol. 10, No. 5, 2013, pp. 407-409.
Shen et al., Tuning the Erosion Rate of Artificial Protein Hydrogels Through Control of Network Topology, Nature Materials, vol. 5, No. 2, Feb. 2006, pp. 153-158.
Shi et al., Polymeric Hydrogels for Post-Operative Adhesion Prevention: A Review, Materials Express, vol. 7, No. 6, Dec. 2017, pp. 417-438.
Song et al., Peritoneal Adhesion Prevention with a Biodegradable and Injectable N,O-Carboxymethyl Chitosan-Aldehyde Hyaluronic Acid Hydrogel in a Rat Repeated-Injury Model, Scientific Reports, vol. 6, No. 37600, Nov. 21, 2016, pp. 1-13.
Stapleton et al., Abstract 21311: A Novel, Shear-Assembling, Shear-Thinning Polymer-Nanoparticle Hydrogel Diminishes Post-Operative Thoracic Adhesions in a Rodent Model of Ischemic Cardiomyopathy, Circulation, vol. 136, No. 1, Jun. 9, 2018, 6 pages.
Stephan et al., Bipolymer Implants Enhance the Efficacy of Adoptive T-cell Therapy; Nature Biotechnology, Nature Biotechnology, vol. 33, No. 1, Jan. 2015, pp. 97-101.
Tamesue et al., Linear Versus Dendritic Molecular Binders for Hydrogel Network Formation with Clay Nanosheets: Studies with Aba Triblock Copolyethers Carrying Guanidinium Ion Pendants, Journal of the American Chemical Society, vol. 135, No. 41, Oct. 3, 2013, pp. 15650-15655.
Vashist et al., Hydrogels: Smart Materials for Drug Delivery, Oriental Journal of Chemistry, vol. 29, No. 3, Nov. 5, 2013, pp. 861-870.
Waldmann et al., Safety (Toxicity), Pharmacokinetics, Immunogenicity, and Impact on Elements of the Normal Immune System of Recombinant Human Il-15 in Rhesus Macaques, Blood, The Journal American Society Hermatology, vol. 117, No. 18, 2011, pp. 4787-4795.
Wang et al., High-Water-Content Mouldable Hydrogels by Mixing Clay and a Dendritic Molecular Binder, Nature, vol. 463, No. 7279, Jan. 21, 2010, pp. 339-343.
Wang et al., PLGA-Chitosan/PLGA-Alginate Nanoparticle Blends as Biodegradable Colloidal Gels for Seeding Human Umbilical Cord Mesenchymal Stem Cells, Journal of Biomedical Materials Research Part A, vol. 96, No. 3, Mar. 1, 2011, pp. 520-527.

Webber et al., Supramolecular Biomaterials, Nature Materials, vol. 15, No. 1, Jan. 2016, pp. 13-26.
Wong Po Foo et al., Two-Component Protein-Engineered Physical Hydrogels for Cell Encapsulation, Proceedings of the National Academy of Sciences of the United States of America, vol. 106, No. 52, Dec. 29, 2009, pp. 22067-22072.
Xu et al., Genetically Engineered Block Copolymers: Influence of the Length and Structure of the Coiled-coil Blocks on Hydrogel Self-assembly, Pharmaceutical Research, vol. 25, No. 3, Mar. 1, 2008, pp. 674-682.
Xu et al., Reversible Hydrogels from Self-Assembling Genetically Engineered Protein Block Copolymers, Biomacromolecules, vol. 6, No. 3, 2005, pp. 1739-1749.
Yamaguchi et al., Photoswitchable Gel Assembly Based on Molecular Recognition, Nature Communications, vol. 3, No. 603, Jan. 3, 2012, pp. 1-5.
Yamaguchi et al., Self-assembly of Gels Through Molecular Recognition of Cyclodextrins: Shape Selectivity for Linear and Cyclic Guest Molecules, Macromolecules, vol. 44, No. 8, Mar. 25, 2011, pp. 2395-2399.
Yang et al., A Postoperative Anti-Adhesion Barrier Based on Photoinduced Imine-Crosslinking Hydrogel with Tissue-Adhesive Ability, Acta Biomaterialia, vol. 62, Oct. 15, 2017, pp. 199-209.
Yeo et al., Polymers in the Prevention of Peritoneal Adhesions, European Journal of Pharmaceutics and Biopharmaceutics, vol. 68, No. 1, Jan. 2008, pp. 57-66.
Yu et al., Comparative Studies of Thermogels in Preventing Post-Operative Adhesions and Corresponding Mechanisms, Biomaterials Science, vol. 2, No. 8, 2014, pp. 1100-1109.
Yu et al., Physical Networks from Entropy-Driven Non-Covalent Interactions, Nature Communications, vol. 12, No. 746, Feb. 2021, pp. 1-9.
Yu et al., Scalable Manufacturing of Biomimetic Moldable Hydrogels for Industrial Applications, Porceedings National Academy Sciences, vol. 113, No. 50, Dec. 13, 2016, pp. 14255-14260.
Zhang et al., Biodegradable and Thermoreversible PCLA-PEG-PCLA Hydrogel as a Barrier for Prevention of Post-Operative Adhesion, Biomaterials, vol. 32, No. 21, Jul. 2011, pp. 4725-4736.
Zhu et al., Metal and Light Free "Click" Hydrogels for Prevention of Post-Operative Peritoneal Adhesions, Polymer Chemistry, vol. 5, No. 6, Feb. 2014, pp. 2018-2026.

* cited by examiner functional polymeric
precursors supramolecular
hydrogel transient
crosslinks Infarct induction
with suture Administration of
Physical Hydrogel

FIG. 3A          FIG 3B

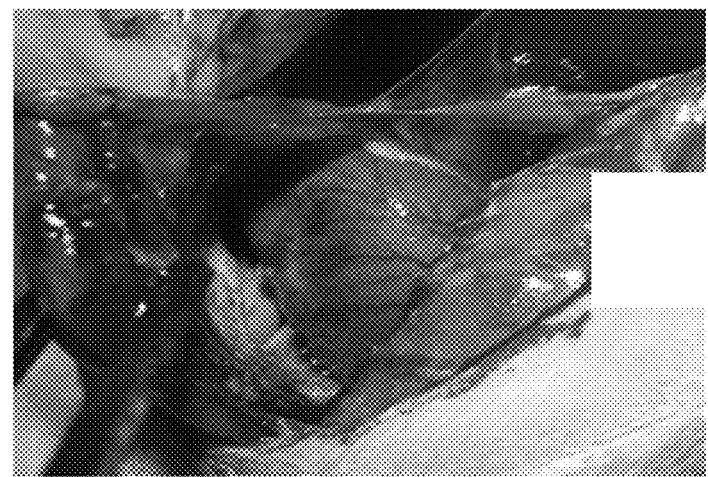
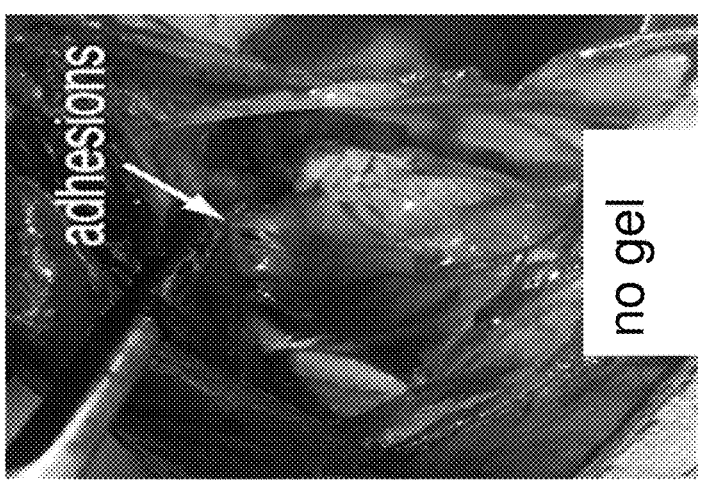
FIG. 4

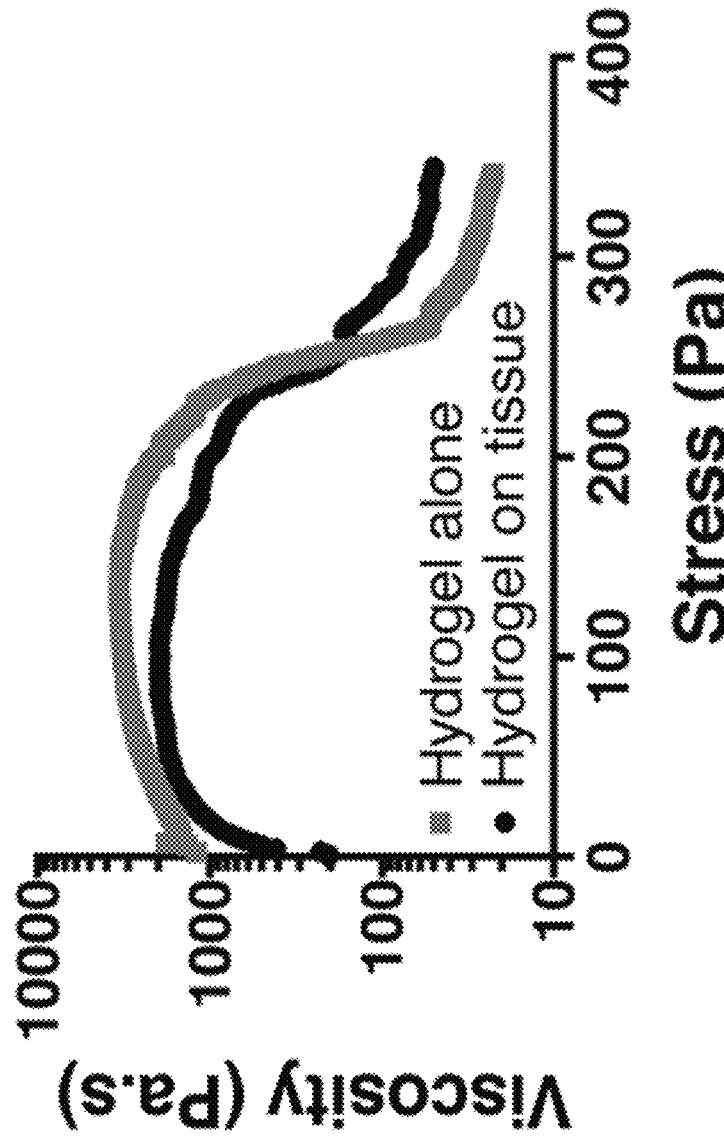
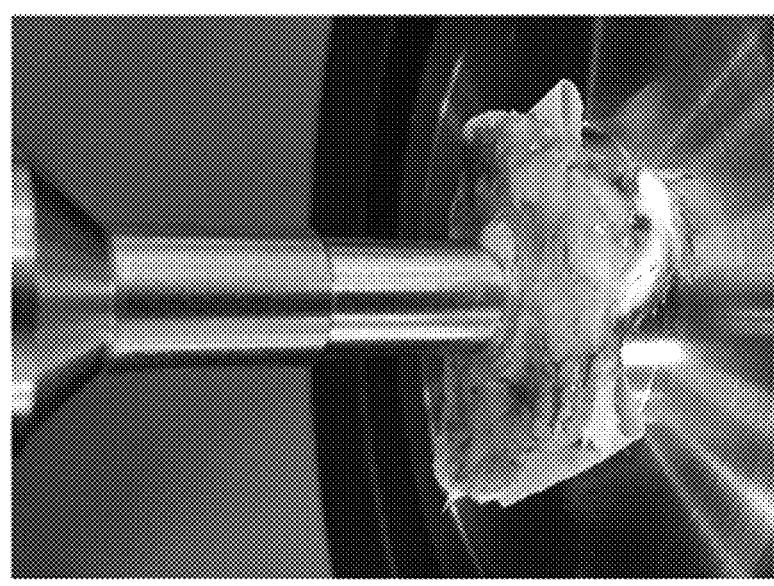
FIG. 6

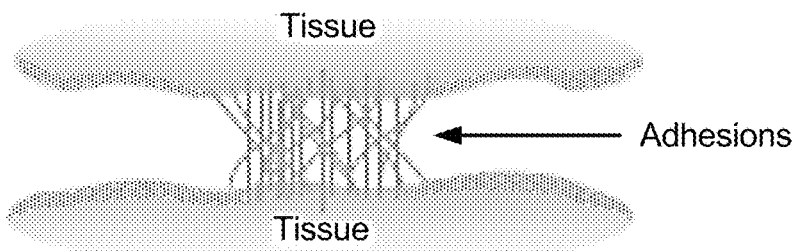
FIG. 14A
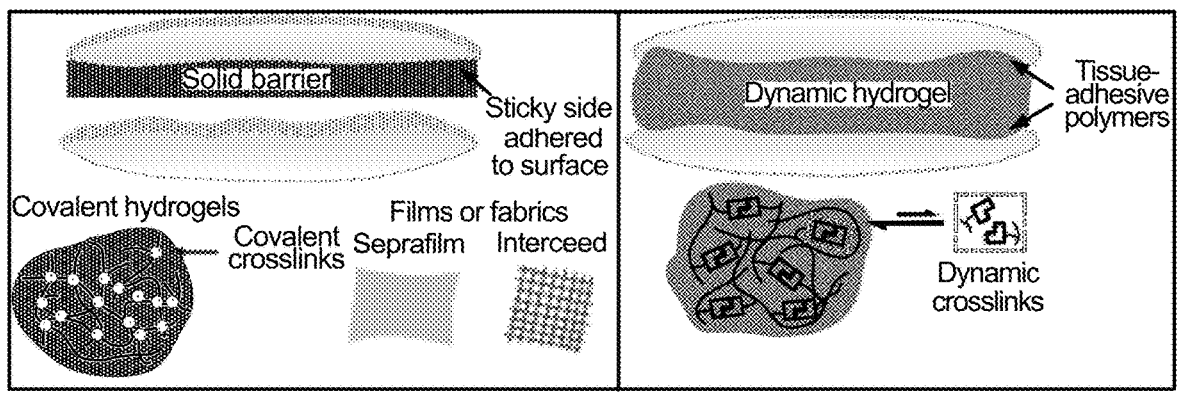
FIG. 14B          FIG. 14C
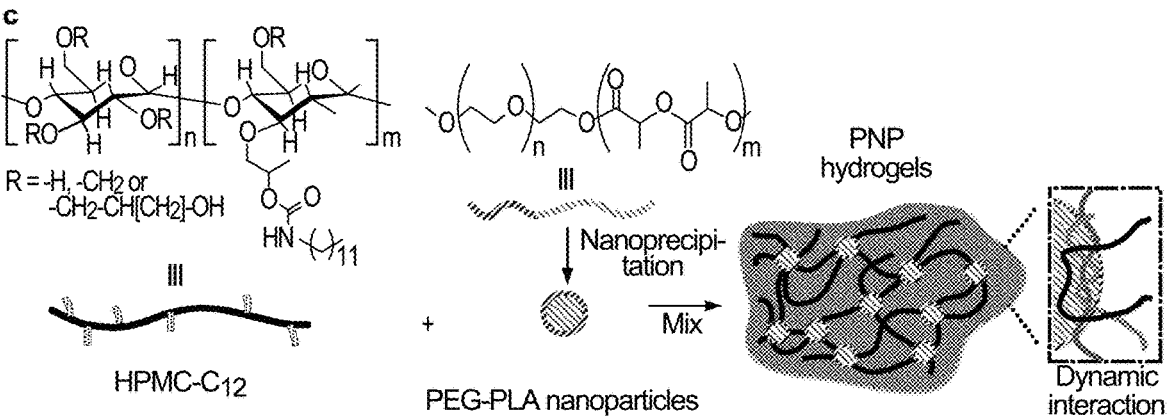
FIG. 14D

Infarct induction
with suture

Administration of
Interceed® or Seprafilm®

Administration of
Physical Hydrogel

Epicardial surface where
hydrogel was administered

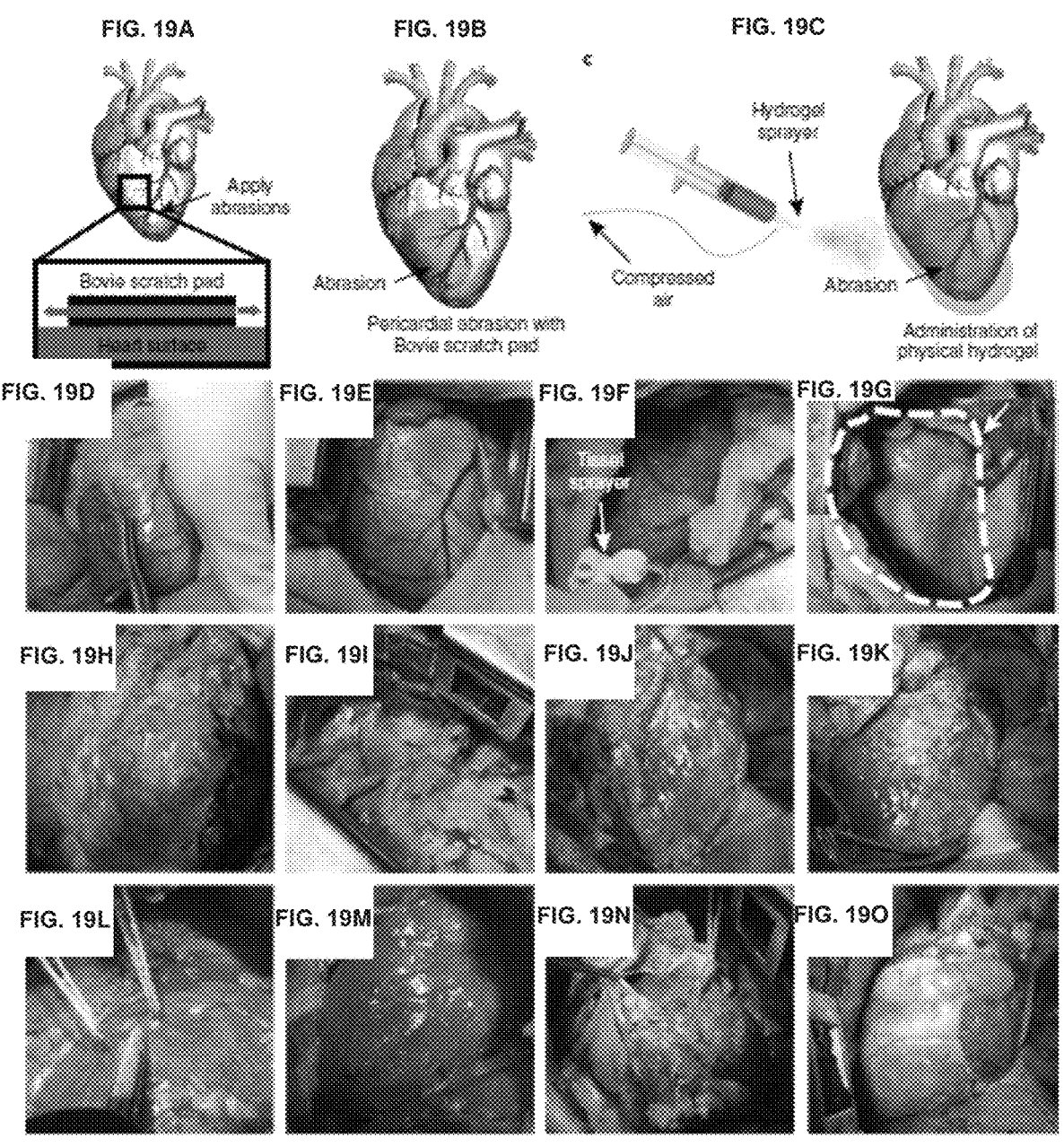

FIG. 20

ADHESION PREVENTION WITH SHEAR-THINNING POLYMERIC HYDROGELS

CROSS REFERENCE TO RELATED APPLICATIONS

This application is a continuation of U.S. patent application Ser. No. 16/590,189, filed Oct. 1, 2019, and titled "ADHESION PREVENTION WITH SHEAR-THINNING POLYMERIC HYDROGELS," which claims priority to U.S. Provisional Application No. 62/739,550, filed Oct. 1, 2018, and titled "ADHESION PREVENTION WITH SHEAR-THINNING POLYMERIC HYDROGELS," and which is a continuation-in-part of U.S. patent application Ser. No. 15/943,358, filed Apr. 2, 2018, and titled "ADHESION PREVENTION WITH SHEAR-THINNING POLY-MERIC HYDROGELS," which claims priority to U.S. Provisional Application No. 62/480,636, filed Apr. 3, 2017, and titled "ADHESION PREVENTION WITH SHEAR-THINNING POLYMERIC HYDROGELS," the entirety of each of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

FIELD

This invention relates to shear-thinning polymeric hydrogels to prevent adhesions that abnormally form between internal organs and tissues following surgery, infections, and other types of bodily insult.

BACKGROUND

Adhesions are fibrous bands of scar tissue that abnormally form between internal organs and tissues following surgery, infections, and other types of bodily insult.

Over 20 million Americans undergo invasive surgery each year, and adhesions develop after 95% of all operations, regardless of the procedure or location on the body. Following abdominal surgery, many patients experience significant post-operative adhesion-related complications, such as severe pain and/or organ dysfunction, with 15-30% requiring a second operation to release the adhesions (i.e., adhesiolysis). In cardiothoracic surgery, 6-17% of all coronary bypass and valve repair/replacement surgeries are reoperations, in which the presence of adhesions significantly lengthens operation times and magnifies the risk of injury to the heart, lung, and great vessels during sternal reentry and cardiac dissection. Patients with congenital heart disease, representing nearly 1% of all live births, commonly require several redo cardiac operations performed over the course of a lifetime, such that 33% of all pediatric and congenital heart surgeries are reoperations. Overall, the annual cost to the U.S. healthcare system for treatment of post-operative adhesions exceeds $2.5 billion, and adhesion-related complications result in nearly 1 million additional days of inpatient care each year, presenting a major unmet clinical need.

Although a vast number of therapeutic agents (e.g., anti-inflammatory drugs), physical barriers, polymers for controlled drug release, and polymeric rheological blends have been studied in the prevention of post-operative adhesions, the prevention of these adhesions remains a significant challenge.

Current solutions available for commercial use are typically polymer films based on polysaccharides and/or synthetic polymers (both resorbable and non-resorbable varieties), which serve as a physical barrier between scarring tissue and surrounding organs. Other technologies that have been tested are based on sprayable pre-polymer solutions that polymerize into polymeric hydrogel films in situ, or which are simple polymer solutions. For polymer solutions comprising, for example, chitosan, hyaluronic acid (HA) and/or carboxymethylcellulose (CMC), the residence time at the injured tissues is too short. For resorbable solid membranes including HA-CMC (SEPRAFILM®, Genzyme, Cambridge, MA) and polylactide, it is difficult to completely cover the affected tissues during application, which is particularly problematic in areas of the body with many surfaces that may form adhesions, such as in the abdomen. Despite the overwhelming need, current adhesion barrier technologies have not been widely adopted due to their inefficacy to fully limit adhesions, rapid degradation time, and difficulty handling during surgery. The present invention advances the art and introduces a different adhesion prevention technology.

SUMMARY OF THE DISCLOSURE

A tissue adhesion prevention hydrogel is described herein that maintains separation between tissues and organs, thus preventing adhesion formation. The adhesion prevention hydrogel can be shear-thinning, viscoelasticity, and rapid self-healing. In some embodiments, the hydrogel can be a polymer nanoparticle (PNP) hydrogel. In one embodiment, the shear-thinning supramolecular hydrogel comprises hydroxypropylmethylcellulose (HPMC). In one embodiment, the shear-thinning supramolecular hydrogel comprises poly(ethyleneglycol)-block-poly(lactic acid) (PEG-PLA) nanoparticles. The PNP hydrogel described herein can include the following physical characteristics, which may contribute to adhesion prevention:

1. a storage modulus (G') of 10-1000 Pa, for example observed at a frequency of 10 rad/s and at a strain within the linear viscoelastic regime of the material using an oscillatory shear test in a parallel plate rheometer;
2. a yield stress of 1-1000 Pa, for example observed using a stress ramp in a parallel plate rheometer;
3. a linear viscoelasticity maintained at strains up to at least 0.5%, for example observed in an oscillatory strain amplitude sweep observed at a frequency of 10 rad/s in a parallel plate rheometer; and
4. a Tan Delta (defined as the ratio of the loss modulus over the storage modulus, G''/G') of less than 1, for example when observed in an oscillatory shear test at a frequency of 10 rad/s and a strain within the linear viscoelastic regime of the material using a parallel plate rheometer.

Described herein is also a method of using the tissue adhesion prevention hydrogel for tissue adhesion prevention.

In general, in one embodiment, a method of preventing tissue adhesion includes: (1) forming an incision in tissue, (2) applying a hydrogel to tissue through the incision, and (3) closing the incision with the hydrogel therein. The hydrogel includes a polymer non-covalently cross-linked with a plurality of nanoparticles and prevents a formation of adhesions between tissues and/or organs.

This and other embodiments can include one or more of the following features. The incision in tissue can be part of a surgical procedure. The polymer can be a cellulose derivative. The polymer can include hydroxypropylmethylcellulose (HPMC). The nanoparticles can include poly(ethylene glycol)-b-poly(lactic acid) (PEG-PLA). The hydrogel can remain on the tissue for at least 7 days after closing the incision. The hydrogel can remain on the tissue for at least 14 days after closing the incision. The hydrogel can dissipate from the tissue in less than 120 days after closing. The hydrogel can dissipate from the tissue in less than 30 days after closing. Applying can include spraying the hydrogel onto the tissue. Applying can include spreading the hydrogel onto the tissue. Applying can include injecting the hydrogel onto the tissue. Applying can include applying shear to the hydrogel to allow the hydrogel to achieve viscous flow so as to conform to and cover the tissue. The hydrogel can adhere to the tissue without delaminating after conforming to and covering the tissue. The hydrogel can stop flowing and can recover its mechanical properties within 5 seconds after applying shear. The tissue can include abdominal tissue. The tissue can include orthopedic tissue. The tissue can include thoracic tissue. The tissue can include cardiac tissue. The tissue can include gynecologic tissue. A storage modulus of the hydrogel can be 50-500 Pa. A yield stress of the hydrogel can be 50-500 Pa. The hydrogel can maintain a linear viscoelasticity at strains up to at least 0.5%. A tan delta of the hydrogel can be less than 1. The hydrogel can be shear-thinning. The hydrogel can be self-healing. The hydrogel can include 1 wt % of the polymer or more. The hydrogel can include 5 wt % of the nanoparticles or more. The hydrogel can include approximately 1 wt % of the polymer and 10 wt % of the nanoparticles.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 4 shows representative images of an untreated heart post-infarction with significant adhesions (left) and a treated heart post-infarction showing no adhesions (right). The bar chart showing the clinical severity ranking for adhesions in rats untreated and treated with the shear-thinning hydrogel according to the present invention.

FIG. 5A shows a schematic illustration of induced myocardial infarction in the heart of a rat, whereby the left anterior descending artery (LAD) is sutured to prevent blood flow to the myocardium, leading to local myocardial infarction. Preliminary studies assessing formation of pericardial adhesions with no treatment or application of either standard-of-care treatments or the anti-adhesion shear-thinning and self-healing hydrogel described herein.

FIG. 6 shows mechanical characterization of PNP hydrogel tissue adhesion. The adhesion of PNP hydrogels to tissue (rat hypodermis) is characterized using a yield stress measurement on a rheometer. In these experiments, it was determined that the yield behavior of PNP hydrogels alone in a standard geometry and when on rat hypodermis. The representative data shown for PNP 1:10 hydrogels shows that the yield stress is equivalent whether on tissue or not, indicating that yielding behavior is cohesive and therefore dictated by the gel mechanics.

FIG. 14A is a schematic representation of adhesion formation between two tissues. FIG. 14B is a schematic representation of previous approaches to prevent adhesions utilizing solid adhesion barriers to physically separate organs and tissues. Such stationary adhesion barriers include two commercial products, SEPRAFILM® and INTERCEED® (film or fabric, respectively), or covalently cross-linked hydrogels formed through in situ polymerization of precursor macromers. FIG. 14C is a schematic representation of the approach described herein that utilizes dynamically-cross-linked, shear-thinning, self-healing, and viscoelastic polymer hydrogels that are placed between organs and tissues, allowing these structures to move naturally. FIG. 14D shows how the PNP hydrogel material described herein exploit multivalent and dynamic non-covalent interactions between hydrophobically-modified hydroxypropylmethyl-cellulose (HPMC-$C_{12}$) and poly(ethylene glycol)-block-poly(lactic acid) (PEG-PLA) to form hydrogels that can be sprayed through standard equipment, adhere to tissue (HPMC-$C_{12}$ is tissue adhesive), and provide a viscoelastic barrier between organs and tissues to inhibit adhesion formation.

FIG. 17A shows pearl live imaging of NIR-797-labelled PNP 1:10 hydrogel in the thoracic cavity following a thoracotomy, myocardial infarction and NIR-797-labelled PNP hydrogel administration. FIG. 17B shows in vivo retention over time of the various PNP hydrogel formulations indicated by relative fluorescence intensity. FIG. 17C shows the area under the curve values generated from the relative intensity curves in FIG. 17B. Data are presented as mean±s.d. Statistical significance was determined by one-way ANOVA with multiple comparisons. NS, not significant; n refers to biological replicates.

FIG. 18A is a representative 10×H&E image of the infarct region of an untreated heart 4 weeks following myocardial infarction (left), and representative 20× image (right).

FIGS. 19A-O show the prevention of adhesion in an epicardial abrasion model in sheep. FIG. 19A is a schematic representation of epicardial abrasion using a Bovie scratch pad. FIG. 19B is a schematic representation of epicardial abrasion to induce local inflammation, leading to formation of severe adhesions. FIG. 19C is a schematic representation of administration of PNP 1:10 hydrogel by spraying onto the heart. FIGS. 19D and E are images of a sheep heart during epicardial abrasion (E) and immediately following abrasion showing inflamed ventricular tissue before closure (F). FIG. 19F is an image of a PNP 1:10 hydrogel being sprayed onto the epicardial surface. FIG. 19G is an image of PNP 1:10 hydrogel coating the epicardial surface immediately before closure. FIG. 19H is a representative image of a human heart during a redo surgery before heart dissection, showing ubiquitous and severe adhesions arising from the previous surgery. FIG. 19I is an image of adhesion formation in control sheep before heart dissection, indicating the presence of severe adhesions similar to those observed in humans and verifying the validity of the large-animal model. FIG. 19J is an image of pericardium and adhesion removal on a sheep heart four weeks following epicardial abrasion with no treatment. FIG. 19K is an image of an untreated sheep heart after dissection. FIG. 19L is an image of pericardium and adhesion removal of a sheep heart four weeks after epicardial abrasion and treatment with SEPRA-FILM®. FIG. 19M is an image of a sheep heart treated with SEPRAFILM® following dissection. FIG. 19N is an image of pericardium removal four weeks following epicardial abrasion and treatment with PNP 1:10 hydrogel. FIG. 19O is an image of a sheep heart treated with PNP 1:10 hydrogel following dissection, showing the absence of adhesions and a pristine, untouched appearance. Sample size for all groups is n=1.

FIG. 20 is a schematic of a PNP (NIR 797-labeled HPMC-C$_{12}$) used for the in vivo retention studies. 60 mg of HPMC-C$_{12}$ was dissolved in 1.6 mL of NMP containing 10 uL of pyridine. 5 mg of NIR 797 isothiocyanate was added to the solution, followed by 4 mg of dibutyltin dilaurate, and left to stir for a minimum of 4 h. The NIR-HPMC-C$_{12}$ sample was dissolved in MilliQ water at 3 wt % concentration, and the fluorescence intensity measured at 800 nm.

FIG. 22A shows an image of the aortic arch and right atrium central cannulation and pulmonary artery venting catheter to decompress the left ventricle. FIG. 22B shows the aortotomy performed to mimic standard aortic valve procedure. FIG. 22C shows the closed aortotomy. FIG. 22D shows the PNP 1:10 hydrogel coating the epicardial surface before closure. FIG. 22E is a representative image (n=3) of an untreated sheep heart after dissection. FIG. 22F is a representative image (n=3) of a sheep heart treated with SEPRAFILM®, following dissection. FIG. 22G is a representative image (n=3) of a sheep heart treated with PNP 1:10 hydrogel, following dissection. FIG. 22H shows blinded clinical scoring of adhesion formation four weeks following cardiopulmonary bypass. Data presented as mean±s.d. (n=3 per group). Statistical significance was determined using a two-tailed Student's t-test against untreated controls. n refers to biological replicates.

DETAILED DESCRIPTION

An adhesion barrier (i.e., a barrier to scar tissue formation) is described herein that can advantageously include one or more of the following properties: (i) tunable shear-thinning and rapid self-healing to enable spraying or spreading on the tissue of interest, (ii) tissue adherence to ensure local retention over clinically-relevant timeframes, (iii) high degree of biocompatibility, and (iv) viscoelasticity to allow organs and tissues to freely move relative to one another to effectively prevent adhesions (FIGS. 14A-D).

Figure 1:
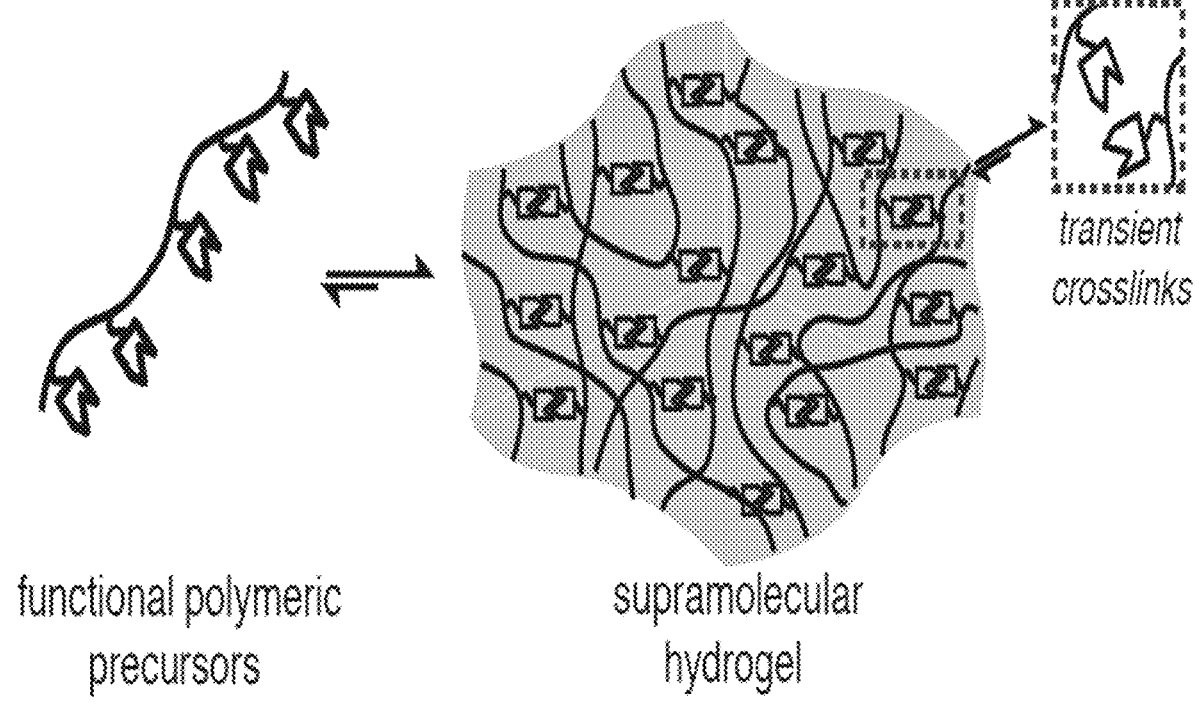
FIG. 1 shows a schematic representation of supramolecular hydrogel systems utilizing functional polymer precursors. These hydrogel materials are shear-thinning and self-healing on account of transient, non-covalent cross-linking between polymer chains.
Figure 2:
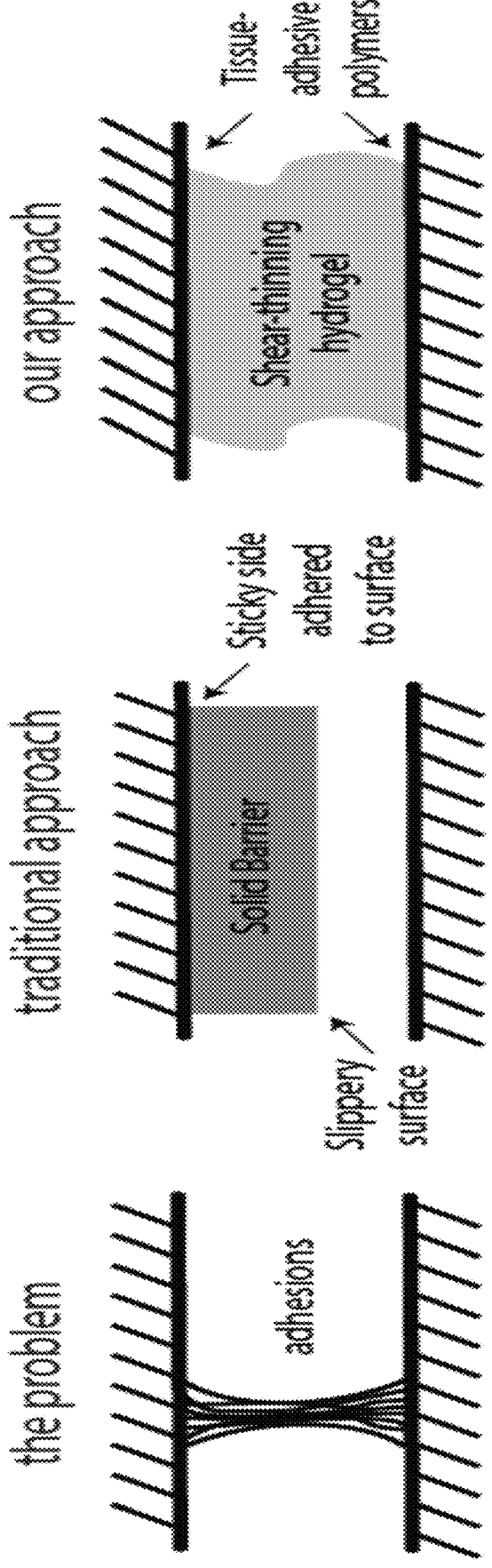
FIG. 2 shows shear-thinning, self-healing, and viscoelastic materials for adhesion prevention. Schematic representation of an adhesion forming between two tissue surfaces (left), traditional solid adhesion barriers (middle) and the approach of the present invention for anti-adhesion technology (right) based on shear-thinning, self-healing polymeric hydrogels. Traditional solid adhesion barriers can often become dislodged and/or degrade too quickly, preventing them from functioning correctly. A platform of dynamically cross-linked supramolecular hydrogels that include hydroxypropylmethylcellulose (HPMC) advantageously allows these materials to adhere well to tissues in the body. These materials can be sprayed, allowing for straightforward application following surgery, while their viscoelastic mechanical properties maintain lubricity between tissues, preventing adhesions.
Figure 23:
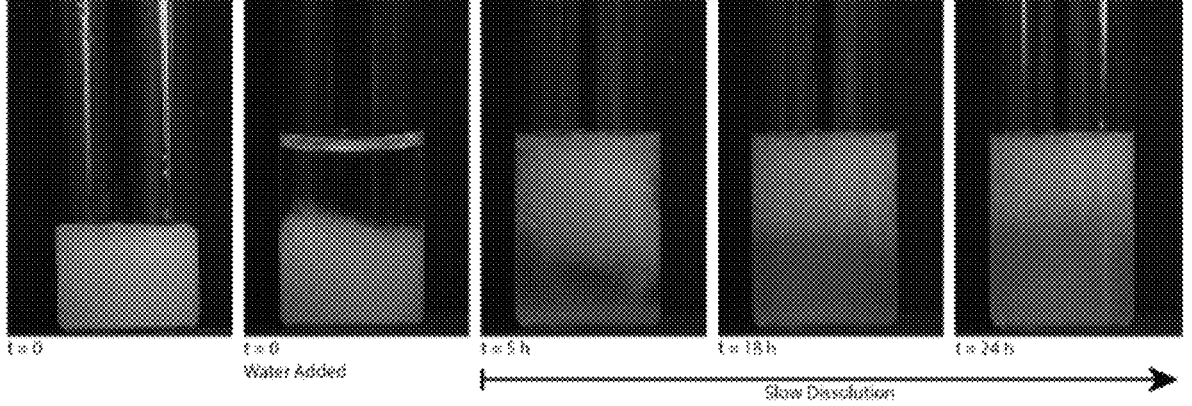
FIG. 23 shows images of a 24 hour time-course swelling assay with PNP 1:10 in water. Over the 24 hour assay period, the PNP 1:10 hydrogel does not swell and slowly dissolves into the water.

In some embodiments, the adhesion barrier can include a supramolecular polymeric hydrogel that constitutes a distinct alternative approach to addressing the critical unmet clinical need for a functional adhesion barrier (FIGS. 14A-D). Utilizing non-covalent interactions (FIG. 1), supramolecular polymeric hydrogels exhibiting viscous flow under shear stress (shear-thinning) and rapid recovery when the applied stress is relaxed (self-healing) can be created. Instead of providing a solid barrier between tissues and organs, the supramolecular hydrogel advantageously creates a shear-thinning and viscoelastic barrier between the two surfaces similar to the body's natural state (FIG. 2). Such supramolecular polymeric hydrogel materials can exhibit highly tunable viscoelastic mechanical properties, shear-thinning, and rapid self-healing, which altogether allows them to be deployed through simple spraying or spreading using standard equipment, or by catheter delivery or direct injection. Further, the supramolecular polymeric hydrogel materials do not appreciably swell like most covalently cross-linked hydrogels, because they typically dissolve as their dynamic crosslinks dissociate (FIG. 23).

In some embodiments, the hydrogel described herein can include 1 wt % or more hydrogel and 5 wt % or more nanoparticles, such as 1 wt % polymer and 10 wt % nanoparticles. Further, the PNP hydrogel described herein can exploit polymer-nanoparticle (PNP) interactions between hydrophobically-modified cellulose derivatives and nanoparticles (NPs). These PNP hydrogels can be formed by a simple mixing of aqueous solutions of dodecyl-modified hydroxypropylmethylcellulose (HPMC-C$_{12}$) with biodegradable polymeric NPs composed of poly(ethylene glycol)-block-poly(lactic acid) (PEG-PLA) (FIG. 14D). In addition, the simplicity of their preparation through a self-assembly process can advantageously allow PNP hydrogel manufacturing to be easily scaled, producing materials with identical mechanical properties. Due to the broadly tunable viscoelastic mechanical properties and excellent biocompatibility of PNP hydrogels, this platform can constitute a simple-to-deploy adhesion barrier to effectively prevent post-operative adhesions.

The tissue adhesion prevention hydrogels described herein can include a shear-thinning and viscoelastic supramolecular hydrogel that comprises cellulose derivatives and nanoparticles. The cellulose derivatives can be hydroxypropylmethylcellulose (HPMC), hydroxyethyl cellulose (HEC), hydroxypropylcellulose (HPC), ethylcellulose (EC), methylcellulose (MC), hydroxyethylmethylcellulose (HEMC), carboxymethylcellulose (CMC), carboxymethyl ethyl cellulose (CMEC), hyaluronic acid (HA), or derivatives. These compounds can be modified with a hydrophobic moiety, such as such as hexyl (—$C_6$), octyl (—$C_8$), decyl (—$C_{10}$), dodecyl (—$C_{12}$), adamantyl, tetradecyl (—$C_{14}$), a saturated or unsaturated alkyl hydrophobic moiety (e.g., $C_{2-18}$, ethyl hexyl), or an aryl hydrophobic moiety (e.g., phenyl, benzyl). The nanoparticles can be a core-shell nanoparticles with hydrophobic cores, such as poly(ethyleneglycol)-block-poly (lactic acid) (PEG-PLA) nanoparticles or poly(ethyleneglycol)-block-poly(caprolactone) (PEG-PCL) nanoparticles.

In some embodiments, PNP hydrogels as described herein can formed by mixing an aqueous solutions of HPMC-x (e.g., 3 wt %) and PEG-PLA NPs (e.g., 15 wt %) in a 1:2 ratio by volume such that the final composition the hydrogel is 1 wt % HPMC and 10 wt % PEG-PLA NPs. These gels formed rapidly upon mixing of the two components.

The anti-adhesion PNP hydrogels described herein may be applied to the tissue of interest following surgery to prevent adhesion. For example, the anti-adhesion hydrogels can be actively spread over the tissue, sprayed over the tissue, injected onto or into the tissue, or expelled onto the surface and allowed to passively spread. Further, the anti-adhesion hydrogel can be sprayed via a nozzle, extruded from a tube, ejected from a syringe or cannula, or delivered through the working channel of an instrument such as a scope (e.g., endoscope or arthroscope).

The anti-adhesion PNP hydrogels described herein can be used in a variety of surgeries to line tissue and prevent adhesions, such as in abdominal surgeries, orthopedic surgeries, gynecologic surgeries, or thoracic surgeries.

Adhesions typically form after surgery and/or surgical incisions for about 7-14 days or 7-10 days. Further, the adhesions typically grow after formation for up to 3 weeks. Thus, in some embodiments, the anti-adhesion PNP hydrogel described herein can be applied to a tissue in the body (e.g., after surgical incision) and can remain on the tissue (e.g., within or proximate to the incision cite) during the time that adhesions typically form and/or grow. Thus, for example, the PNP hydrogel can remains on the tissue for at least 7 days, at least 10 days, at least 14 days, or at least 21 days. Remaining on the tissue for this timeframe can advantageously ensure that the tissue prevent adhesion during the time that adhesions would otherwise form or grow. Further, in some embodiments, the anti-adhesion PNP described herein can dissipate from the tissue after the time frame. For example, the anti-adhesion PNP can be gone or fully dissipated from the tissue in less than 120 days, less than 100 days, less than 50 days, less than 30 days, or less than 20 days from the first time.

Exemplary features of the anti-adhesion hydrogels described here that can help maintain separation between tissues and organs and prevent adhesion formation include: shear-thinning, viscoelasticity, and rapid self-healing (FIGS. 7-13).

As used herein, "viscoelastic" means that the storage modulus (G') is dominant over the loss modulus (G") at some point, for example as observed in an oscillatory frequency sweep measurement in the range of 0.1-100 rad/s on an oscillatory rheometer performed in the linear viscoelastic regime, yet exhibiting complete stress relaxation following application of a constant strain of 500% within 15 minutes.

As used herein, "shear-thinning" means that the viscosity of the gel decreases with increasing shear rate in the range of 0.1-100 cycles/second, for example as observed on an oscillatory rheometer.

As used herein, "self-healing" means that either the modulus or the viscosity recovers at least 90% of its original value within 5 min in a step-strain (conducted with strains of 0.5% and 500%) or step-shear (conducted with shear rates of 0.1 cycles/second and 100 cycles/second) measurement, respectively, on an oscillatory rheometer. In some embodiments, the PNP hydrogel described herein can stop flowing and recover its mechanical properties within 5 seconds after applying shear (e.g., so as to become more solid-like and adhere to the tissue).

Experimental Results 1—Viscoelastic and Flow Properties of PNP Hydrogel

Figures 15A, 15B, 15C, 15D, 15E, 15F, 15G, 15H, 15I:
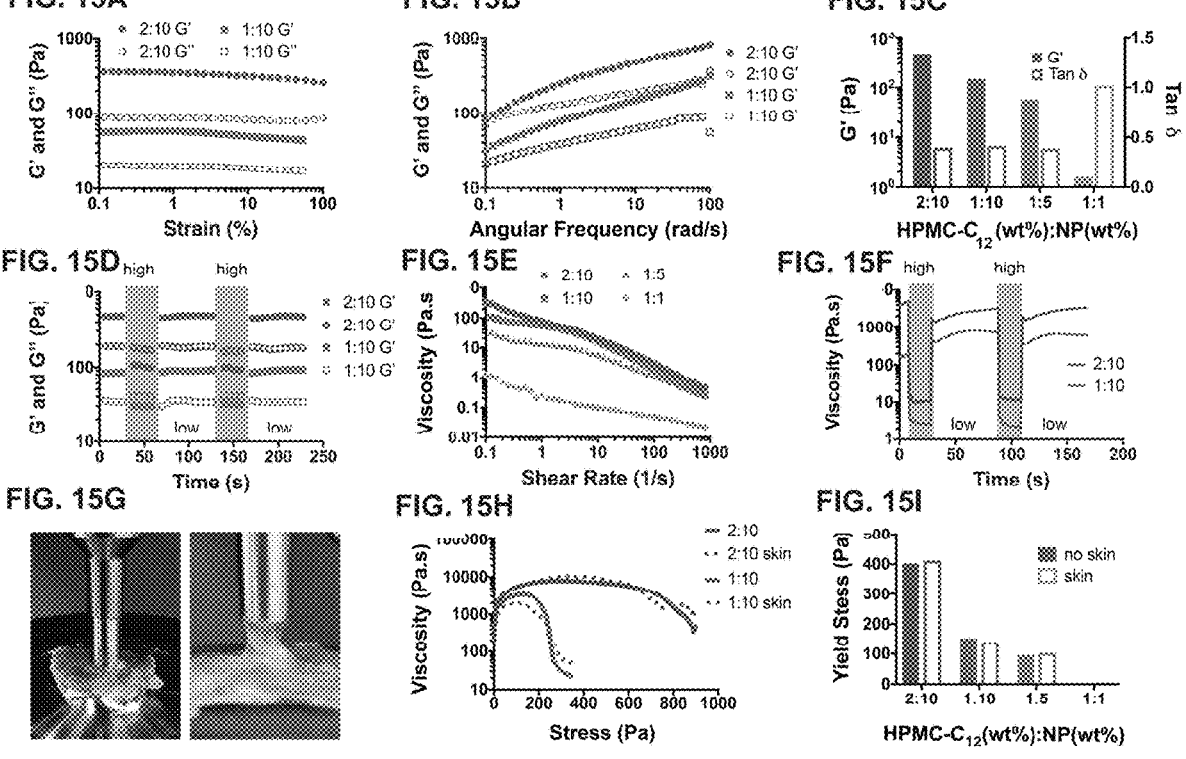
FIG. 15A shows the strain-dependent ($\omega$=10 rad s$^{-1}$, 25° C.) oscillatory shear rheology of PNP hydrogels comprising HPMC-$C_{12}$ and PEG-PLA NPs, denoted wt % HIPMC-$C_{12}$ wt %: NP wt %.
FIG. 15B shows the frequency-dependent ($\varepsilon$=2%, 25° C.) oscillatory shear rheology of PNP hydrogels comprising HPMC-$C_{12}$ and PEG-PLA NPs, denoted wt % HIPMC-$C_{12}$ wt %: NP wt %.
FIG. 15C shows an overview of oscillatory rheological properties of a series of PNP hydrogels ($\omega$=10 rad s$^{-1}$, $\varepsilon$=2%, 25° C.).
FIG. 15D shows the step-strain measurements of PNP 1:10 and 2:10 hydrogel formulations with high strains (destructive; 750%) and low strains (restorative; 0.5%) to characterize extent and rate of stationary self-healing.
FIG. 15E shows the steady shear rheology of various PNP hydrogel formulations as described herein demonstrating highly shear-thinning behavior.
FIG. 15F shows step-shear measurements of PNP 1:10 and 2:10 hydrogel formulations with high shear (100 s$^{-1}$) and low shear (0.1 s$^{-1}$) to characterize the extent and rate of flow-based self-healing.
FIG. 15G is an image of the experimental setup utilized to determine adhesion of PNP hydrogels to tissue (rat hypodermis).
FIG. 15H shows the yield stress behavior of PNP 2:10 and 1:10 hydrogels in a standard parallel plate geometry and on rat hypodermis in a stress ramp experiment performed at a rate of approximately 1.5 Pa s$^{-1}$.
FIG. 15I shows the yield stress values of PNP hydrogel formulations obtained from the peak viscosity observed in the stress ramp.

A series of PNP hydrogels comprising HPMC-$C_{12}$ and PEG-PLA NPs was created by controlling the concentration of both components, where hydrogel formulations are denoted polymer: NP (wt %:wt %). The PNP 1:10 and PNP 2:10 hydrogels used in this study both exhibited solid-like behavior (G' (storage modulus)>G" (loss modulus)) and linear viscoelastic response up to strains exceeding 100% in strain-dependent oscillatory rheological measurements (FIG. 15A). These results indicate that the hydrogels exhibited an extremely broad range of strains over which the solid-like properties are preserved. For reference, the highest strains experienced by tissues in the body are typically about 10%, meaning that the engineered material properties of the hydrogel can be maintained within the dynamic environment in the body. Further, PNP hydrogels exhibited a frequency response that were highly formulation dependent in frequency-dependent oscillatory shear experiments performed in the linear viscoelastic regime (FIG. 15B). For comparison, the storage modulus (G') taken at ω=10 rad/s was used as a measure of hydrogel stiffness, and the tan δ (the ratio of the loss modulus over the storage modulus; tan δ=G"/G') taken at ω=10 rad/s was used as a metric of hydrogel viscoelasticity (FIG. 15C). PNP 1:5, 1:10, and 2:10 maintained solid-like behavior over the entire range of observed frequencies (0.1 to 100 rad/s), while PNP 1:1 and 0.2:10 were fluid-like. Step-strain measurements were performed to demonstrate recovery of the PNPs dynamic material response following network rupture at high strains. High magnitude strains were applied to break the hydrogel structure (ε=750%), which was followed by low magnitude strains (ε=0.5%) to investigate the rate and extent of hydrogel recovery to initial mechanical properties (FIG. 15D). PNP 1:5, 1:10, and 2:10 hydrogels undergo a dramatic change to fluid-like behavior at high strains, indicated by an inversion of G' and G", but rapidly recover (<5 s) their initial solid-like dynamic response when the strain is decreased. This behavior was repeatable over several cycles, indicating that the shear-thinning is driven by the rupture of the non-covalent crosslinks and not through cleavage of covalent bonds within the polymers.

Steady-shear and step-shear measurements were performed to investigate the flow properties of these materials, which are highly relevant to flow-based processes such as spraying, spreading, or injection (FIGS. 15E and 15F). PNP hydrogels were highly shear-thinning (FIG. 15E), reducing their viscosity upwards of three orders of magnitude over shear rates extending from 0.1-100 s$^{-1}$. The recovery of the PNP hydrogel's mechanical properties following network rupture and flow at high shear rates, such as those imposed on the gel when spraying or injecting onto target tissues were measured with step-shear experiments. High shear rates ($100 \text{ s}^{-1}$) followed by low shear rates ($10 \text{ s}^{-1}$) were applied to the hydrogel while monitoring the viscosity (FIG. 15F). Again, the PNP hydrogels shear-thin dramatically at high shear rates, reducing in viscosity by roughly three orders of magnitude, yet quickly recover their viscosity when the shear rate is decreased. Similar to step-strain measurements discussed above, this rapid and complete recovery of mechanical properties is observed over several cycles.

The adhesion of PNP hydrogels to a model tissue, rat hypodermis, was characterized using yield stress measurements (FIG. 15G). In these experiments, the yield behavior of PNP hydrogels alone in a standard geometry and on rat hypodermis was determined. It was assumed that rat hypodermis would be an adequate predictor of PNP adhesion to tissues of interest, such as epicardium, parietal pleura, mucosa, and serosa, on account of the similarity of the tissues. For PNP 2:10 and 1:10 hydrogel formulations, the yield stress of the material is equivalent whether on tissue or not (FIG. 15H), indicative of a cohesive yielding behavior (failure of the gel itself) and not adhesive failure between the hypodermis and gel (FIG. 15I). PNP 1:5, 1:10, and 2:10 hydrogels exhibited formulation-dependent yield stresses that were cohesive in nature, while PNP 1:1 did not exhibit a yield stress, presumably on account of its fluid-like properties.

Experimental Results 2—In Vivo Efficacy in Rodents

Figure 3:
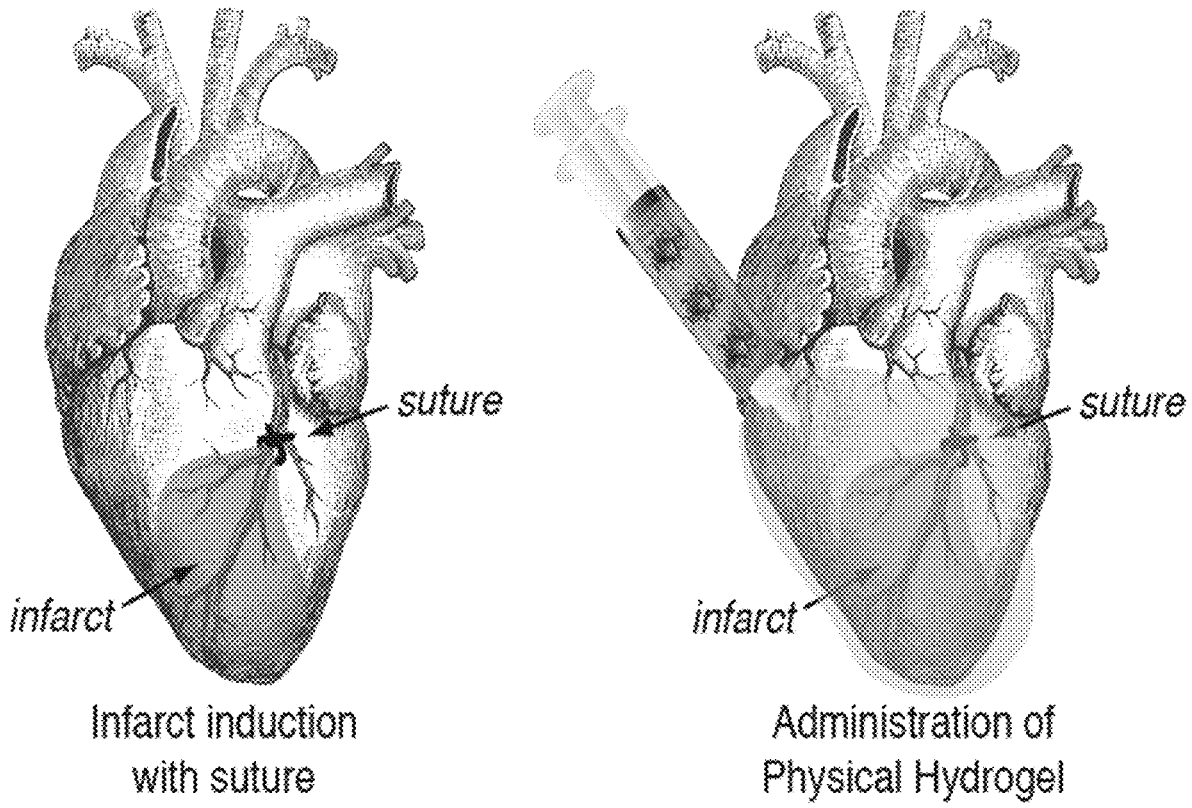
FIG. 3A shows a schematic illustration of the induced myocardial infarction in heart of a rat model whereby the left anterior descending artery is sutured to prevent blood flow to the myocardium, leading to local myocardial infarction.
FIG. 3B shows a schematic illustration of application of anti-adhesion hydrogel including the shear-thinning and self-healing hydrogel according to the present invention and applied to the pericardial region of the heart.
Figure 5A:
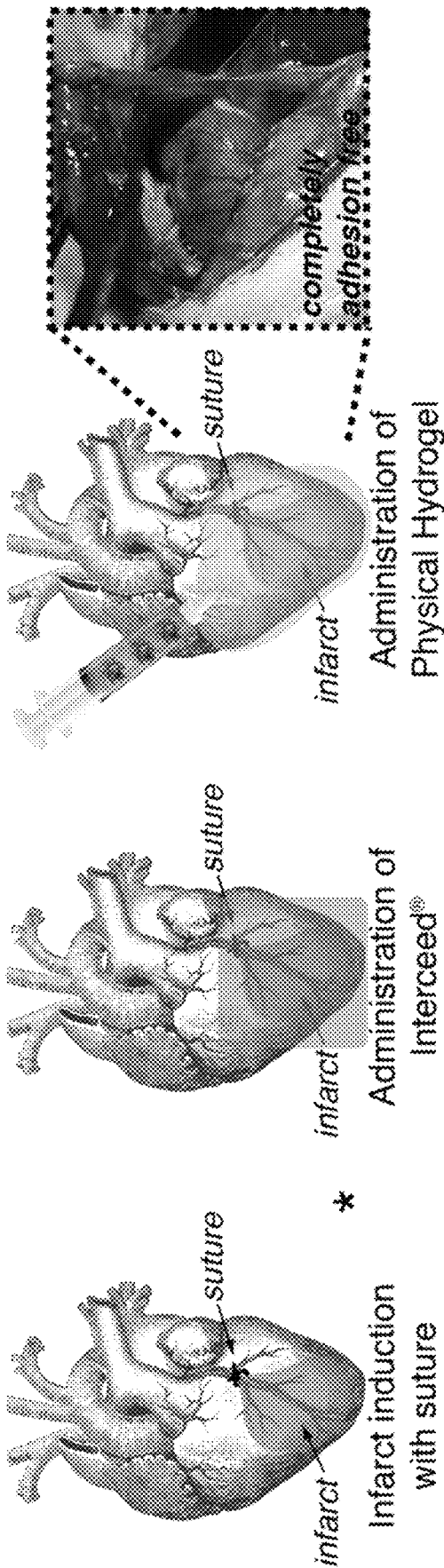
FIG. 5A shows additional teachings and data compared to FIGS. 3A-B and FIG. 4.
Figure 5B:
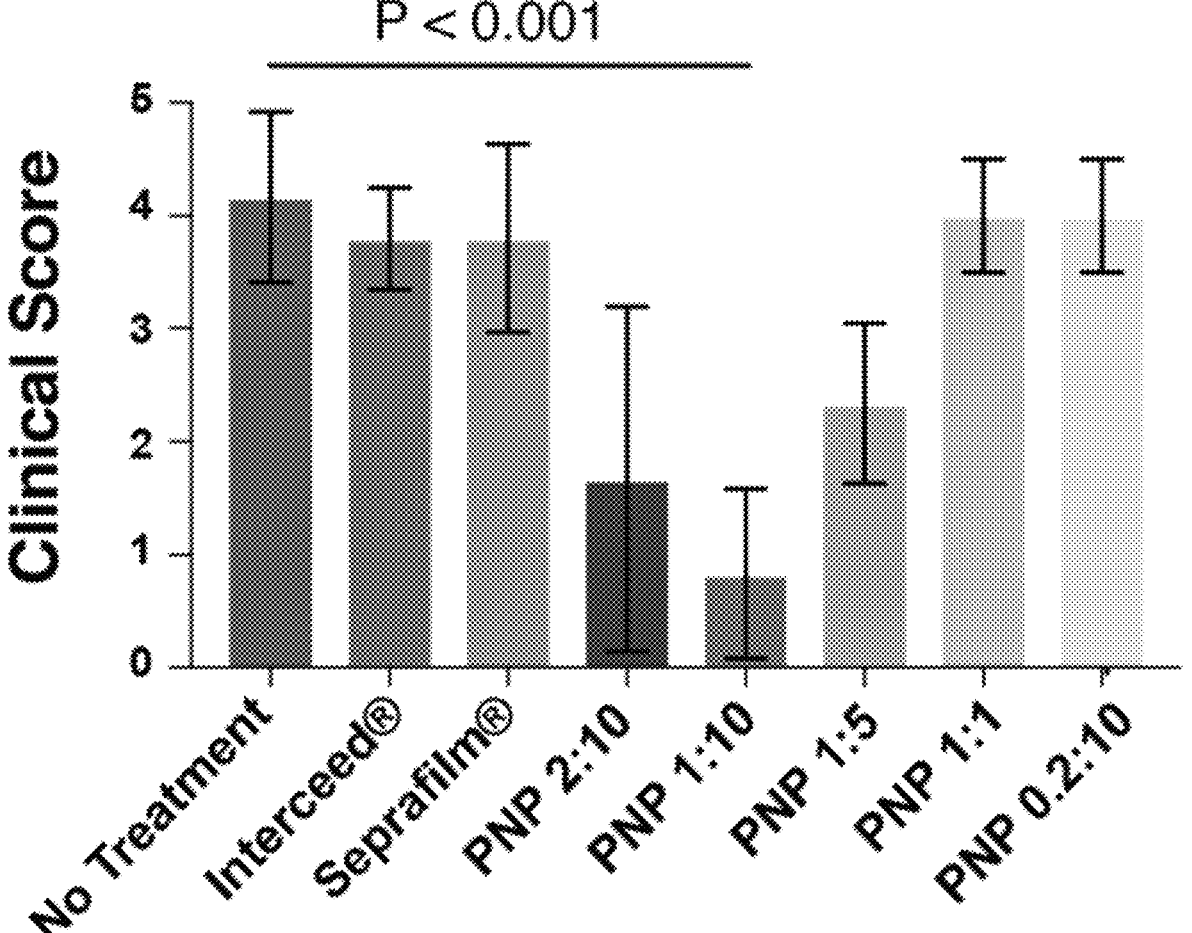
FIG. 5B shows double-blinded clinical scoring of adhesion formation one-month following induction of myocardial infarction demonstrates that application of PNP hydrogels dramatically reduces the incidence and severity of adhesions.
Figure 5C:
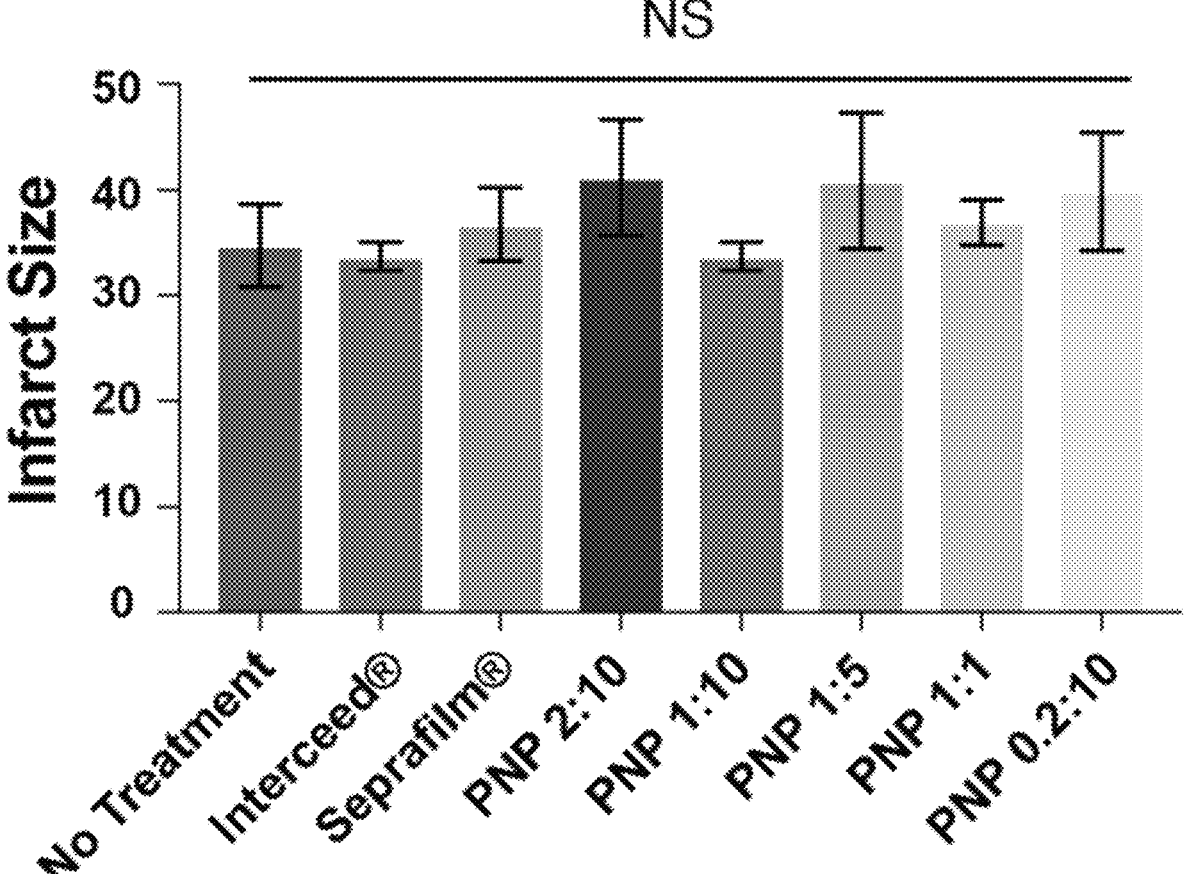
FIG. 5C shows infarct size was used to ensure consistency across groups. Data presented as mean±s.d. (n≥6). PNP formulation denoted as wt % HPMC-$C_{12}$: wt % PEG-PLA NPs (i.e., 1:10 refers to a formulation comprising HPMC-$C_{12}$ at 1 wt % and PEG-PLA NPs at 10 wt %).
Figure 7:
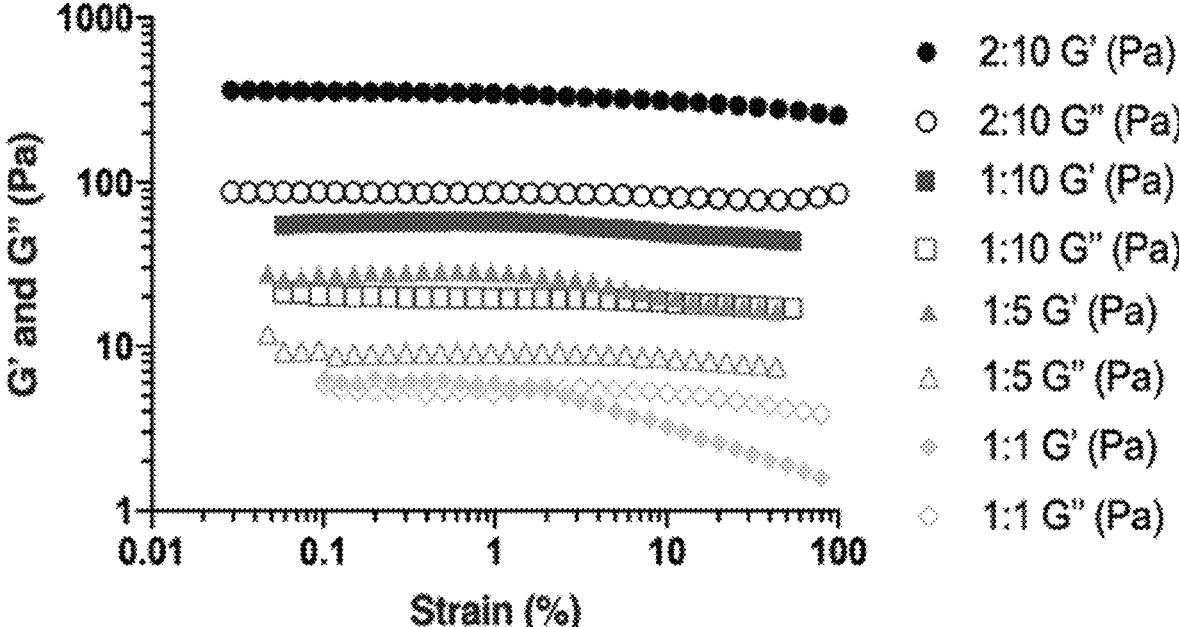
FIG. 7 shows strain-dependent oscillatory shear rheology ($\omega$=10 rad$^{s-1}$, 25° C.).
Figure 8:
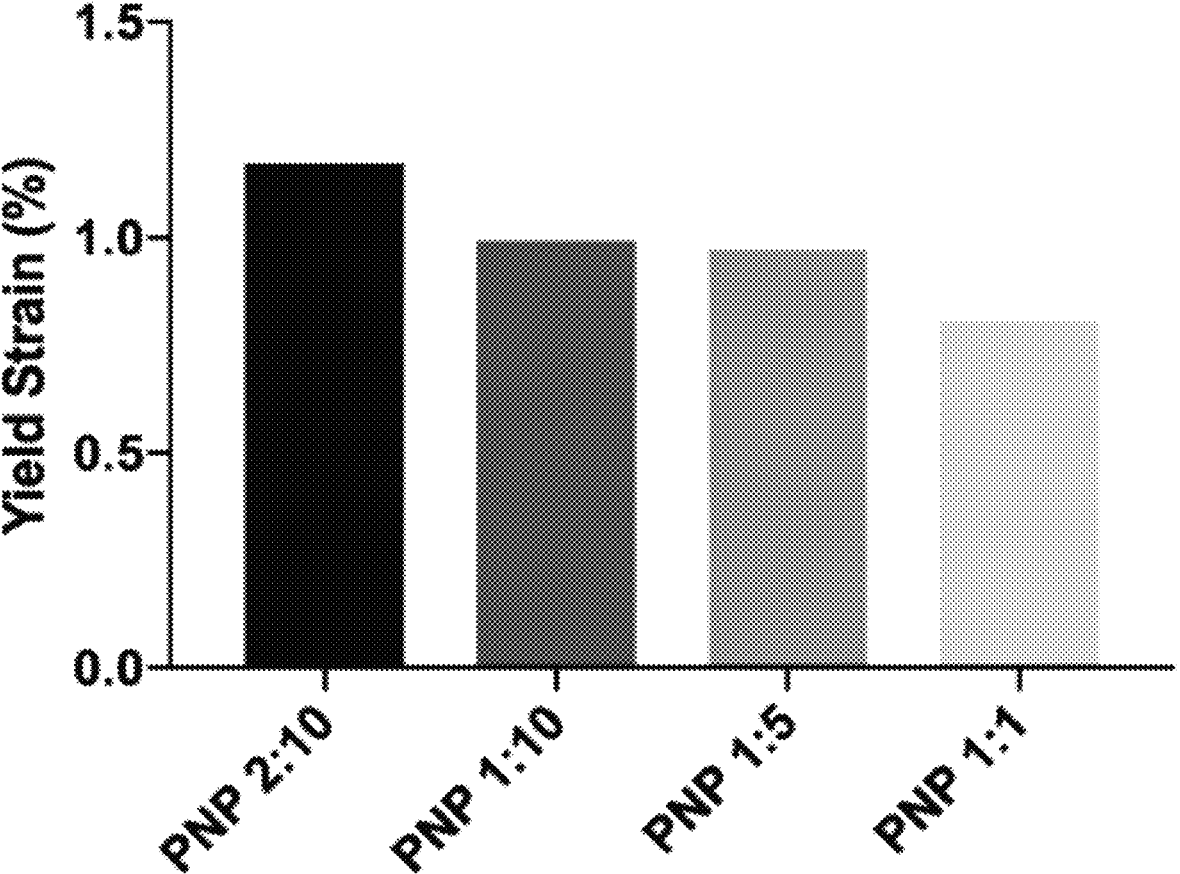
FIG. 8 shows yield strain of PNP hydrogel formulations defined as the stain where the material deviates from the linear viscoelastic regime. Yield strain values are taken from the inflection point where tan δ (G''/G') deviates from linearity.
Figure 9:
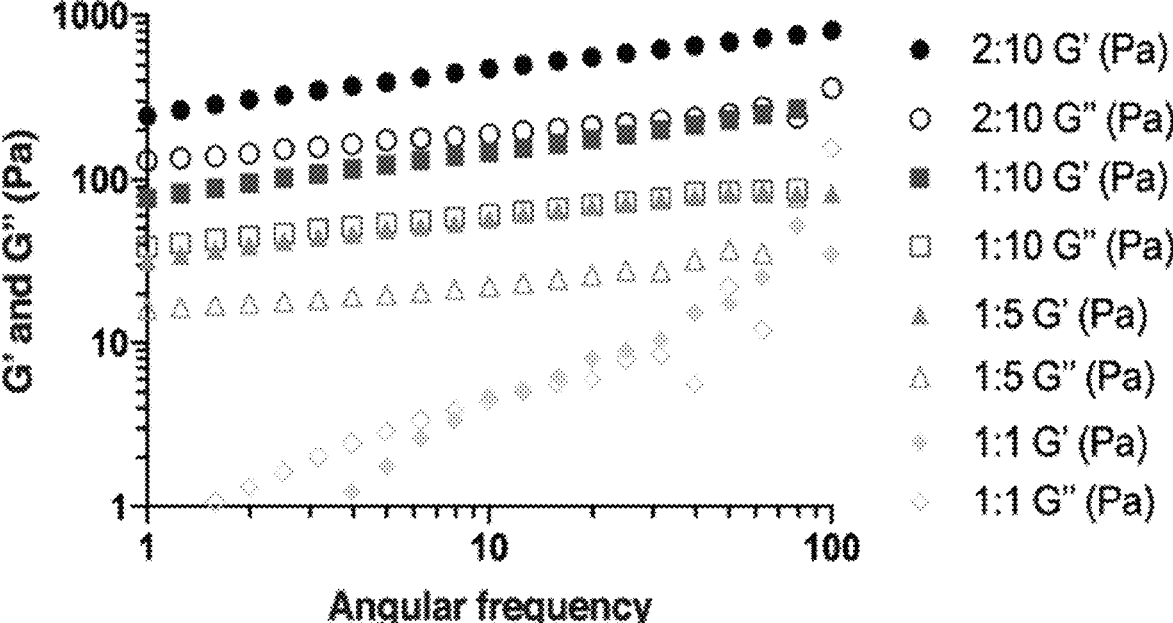
FIG. 9 shows frequency-dependent oscillatory rheology of PNP hydrogels comprising HPMC-$C_{12}$ (x %) and PEG-PLA NPs (x %) (strain amplitude=2%, 25° C.).
Figure 10:
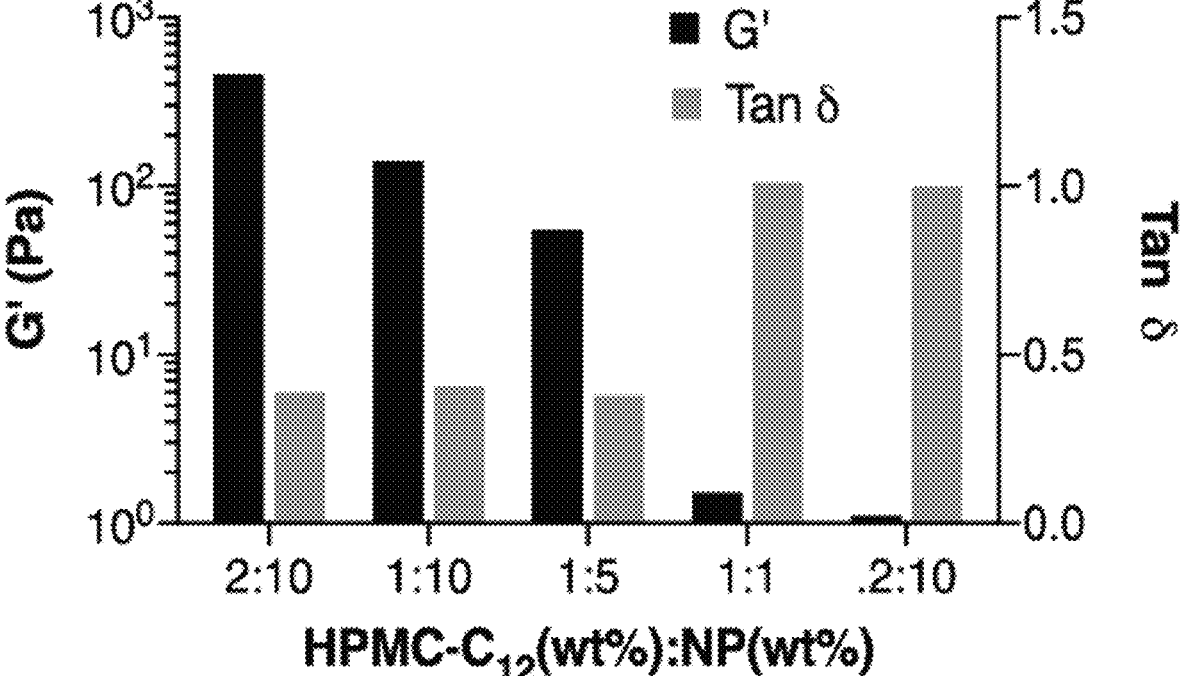
FIG. 10 shows according to an exemplary embodiment of the invention oscillatory rheological properties of hydrogels: storage modulus (G'; a measure of strength) and tan δ (a measure of elasticity) values for different PNP hydrogel formulations.
Figure 11:
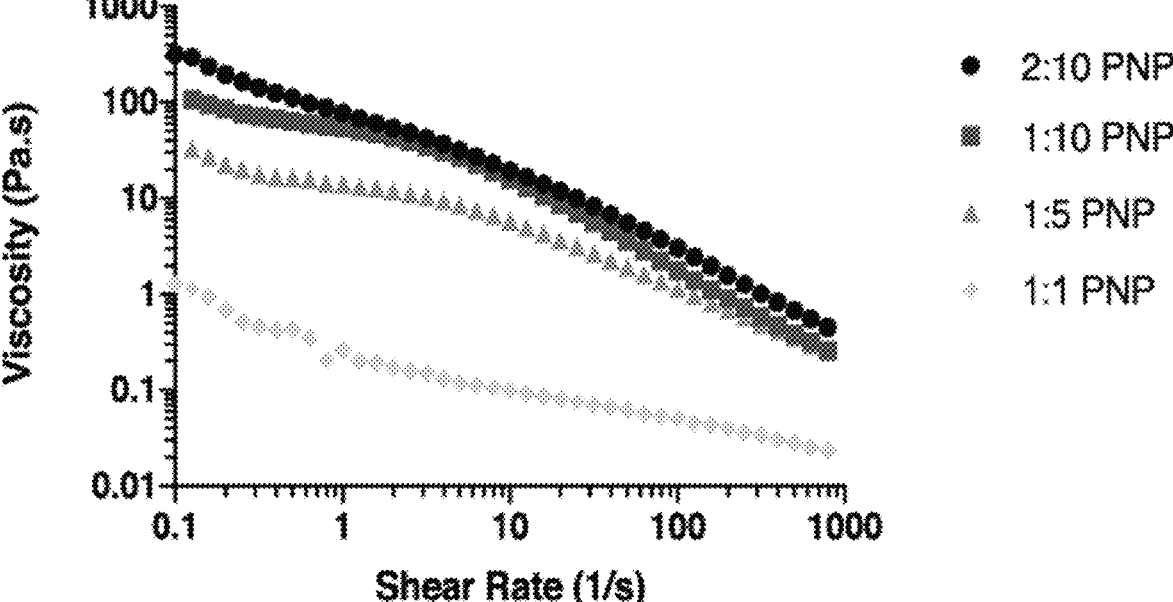
FIG. 11 shows steady shear rheology of different PNP hydrogel formulations.
Figure 12:
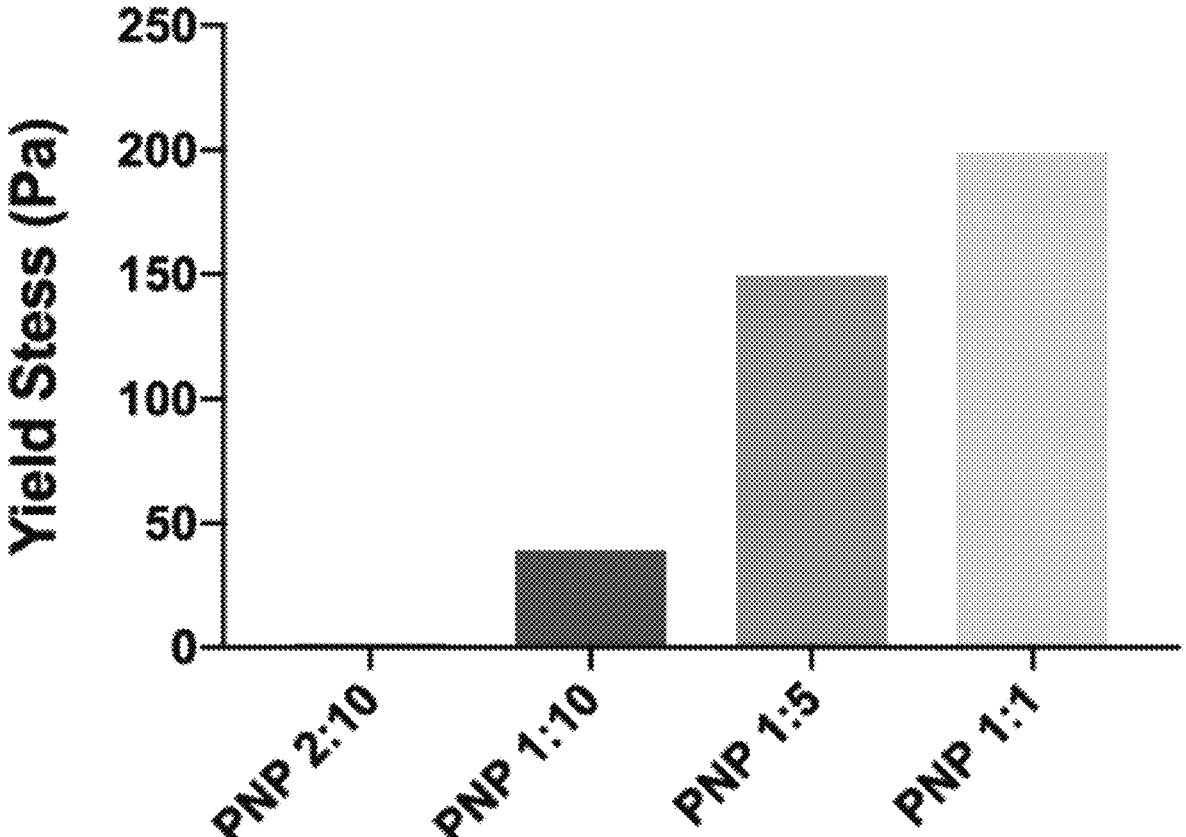
FIG. 12 shows yield stress values of PNP hydrogel formulations obtained from the peak viscosity observed in a stress ramp performed at a rate of approximately 1.5 Pa/s.
Figure 13:
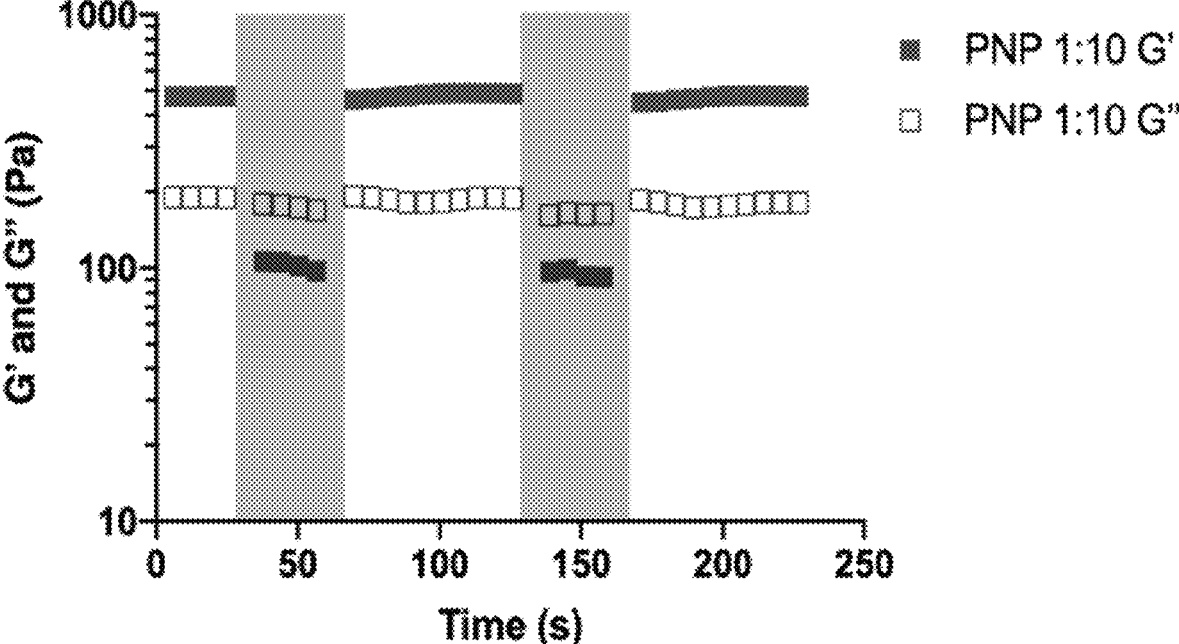
FIG. 13 shows step-strain measurements of PNP hydrogels comprising HPMC-$C_{12}$ (1%) a PEG-PLA NPs (10%), whereby high strains (destructive; 750%) and low strains (0.5%) were alternated to assess the rate of self-healing, indicate that PNP gels completely recover their mechanical properties in less than 5 s.

To demonstrate the utility of PNP hydrogels to prevent adhesions, an established and highly reproducible model of myocardial infarction in rats was used in which mature adhesions are formed in the thoracic cavity following a thoracotomy and myocardial infarction. In these studies, ten Sprague-Dawley rats experienced an induced myocardial infarction in which a thoracotomy is performed and the left anterior descending artery is permanently occluded with a suture producing an anterolateral myocardial infarction (FIG. 3A). The animals were randomized to receive pericardial delivery of 250 microliter of PNP gel surrounding the heart (FIG. 3B) or no treatment for preventing adhesions. Following treatment, the thoracotomy is closed. Rats were sacrificed four weeks later to evaluate the anti-adhesive efficacy utilizing a standard adhesion scoring system on a scale from 0 to 5. The scores of adhesions were taken via a double-blinded process and are reported in FIG. 4. Qualitatively, there was a clearly visible difference in the number and severity of adhesions in the rats that were given treatment and the rats that were not (FIG. 4). In the control group, all rats presented with a score of 4 or 5 with an average score of 4.5, which demonstrates the successful establishment of a repeatable injury model in the thoracic cavity. Furthermore, a significantly lower adhesion score ($P<0.001$) was found in the PNP hydrogel treatment group (FIG. 4). In addition, not only were there minor to no adhesions in the treated group, but no PNP hydrogel residue remained in the thoracic cavity after the 4 week study, which supports the high efficacy of the anti-adhesion capabilities and biodegradation/resorbability of the PNP hydrogel system.

Figures 16A, 16B, 16C, 16D, 16E:
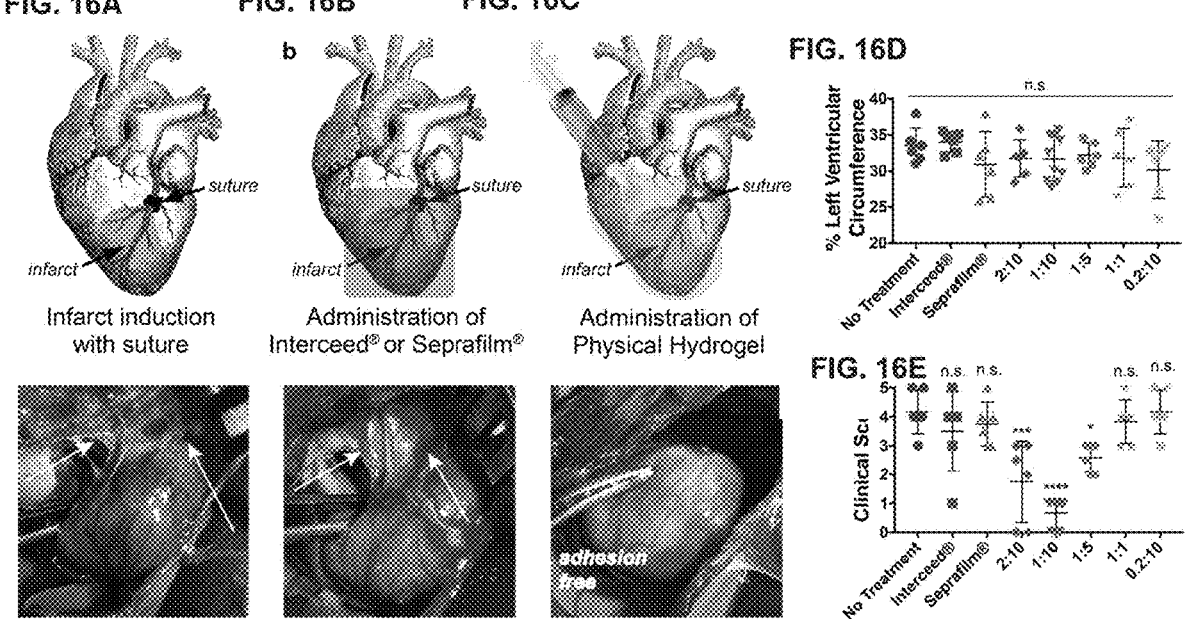
FIG. 16A is a schematic illustration of induced myocardial infarction, whereby the left anterior descending artery (LAD) is ligated to prevent blood flow to the myocardium, leading to local myocardial infarction (top). Representative image of an untreated control heart 4 weeks after infarction (bottom).
FIG. 16B is a schematic illustration of immediate administration of INTERCEED® or SEPRAFILM® (commercial treatment options) following the infarction (top) and representative image of a heart treated with a commercially-available adhesion barrier (bottom), 4 weeks after infarction.
FIG. 16C is a schematic illustration of administration of PNP hydrogels immediately following infarction (top) and a representative image of the in vivo efficacy of PNP hydrogel (1:10), 4 weeks after infarction. The white arrows indicate adhesions.
FIG. 16D shows that infarct size was used as a measure of induced local inflammation to ensure consistency across treatment and control groups.
FIG. 16E shows double-blinded clinical scoring of adhesion formation 4 weeks following induction of the myocardial infarction model. Data presented as mean±s.d. (n≥6). PNP formulation notation indicates loading (wt %) of HPMC-$C_{12}$ and PEG-PLA NPs. Statistical significance was determined against untreated controls.

Experimental Results 3—In Vivo Efficacy in Rodent Model of Pericardial Adhesion Similar to as described above with respect to Experimental Results 2, a rat myocardial infarction model was used to investigate the efficacy of the PNP hydrogel system. The inflammation and tissue damage occurring in this model on account of the infarcted cardiac tissue reproducibly generates robust pericardial adhesions. The myocardial infarction model exhibits a greater incidence of severe adhesions that are more translationally relevant, thus potentially providing a better predictor for a translationally relevant solution. An anterolateral/anterior myocardial infarction was induced in rodents via permanent left anterior descending (LAD) artery ligation (FIG. 16A). Infarct size was controlled in all treatment groups by ligating the LAD at the same location in each surgery. The infarct size was measured by the percent of the left ventricular wall that was infarcted and was kept consistent to ensure all animals experienced similar inflammatory responses and tissue necrosis, which contributes to adhesion formation (FIG. 16D).

Immediately following ligation, rats (n=52) were randomized to receive either (i) one of a series of PNP hydrogels (0.2:10, 1:1, 1:5, 1:10, and 2:10; 200 µL), (ii) commercially available adhesion barriers INTERCEED® or SEPRAFILM® ($1 \text{ cm}^2$), or (iii) no treatment (i.e., control) prior to the closing of the thoracotomy. Rats were sacrificed 4 weeks later to evaluate the anti-adhesive efficacy. A sternotomy was performed to visualize adhesion formation and to assess the in vivo efficacy of the PNP hydrogel treatments (FIG. 16A, 16B, 16C). Using videos and images, adhesion scores were assigned via a standard, double blinded clinical scoring system on a scale from 0 to 5 (FIG. 16E). In this system, a score of zero indicates no adhesions and a score of five indicates a high incidence of severe, vascularized adhesions. Finally, adhesions were removed and the heart explanted for histological analysis.

In the untreated control group, the hearts were completely adhered to the chest wall (FIG. 16A), presenting an adhesion score of 4.2±0.8 and demonstrating the reliability of the myocardial infarction model to form adhesions in the thoracic cavity. Commercial adhesion barrier treatment groups presented with an adhesion score of 3.8±0.8 and 3.3±1.2, which was not different from that of the control groups (FIG. 16B). Animals treated with a PNP hydrogel adhesion barrier exhibited formulation-dependent adhesion scores, likely due to the differences in viscoelasticity and yield stress of the various materials investigated. Solid-like PNP hydrogel formulations (G'>G") 1:5, 1:10, and 2:10 all formed physical adhesion barriers that significantly reduced the incidence and severity of adhesions when compared to the untreated control group, albeit with formulation-dependent efficacy and variability. In contrast, liquid-like PNP formulations (G">G') 0.2:10 and 1:1 did not significantly inhibit adhesions, likely on account of their propensity to flow under low stress.

Notably, PNP 1:10 performed the best as an adhesion barrier, as very minor adhesions, if any, were grossly observed, and animals presented with an adhesion score of 0.6±0.5 (p<0.0001) (FIG. 16c). The PNP 2:10 hydrogel also yielded a low mean adhesion score of 1.8±1.4 and significant efficacy (p<0.001), but considerable variability in results was observed. PNP 1:5 hydrogel also significantly reduced adhesions compared to the control group, presenting with an adhesion score of 2.6±0.4 (p<0.05). These observations indicate that an optimal range of yield stress and/or storage moduli, as demonstrated by the PNP 1:10 hydrogel, results in more effective and sustained coverage of tissue over the 4 week period, effectively preventing adhesions. In addition to the reduction in adhesions observed in the solid-like PNP hydrogel-treated groups, PNP hydrogel residue was completely resorbed by the end-point of the 4 week study.

Experimental Results 4—PNP Hydrogel Retention at the Site of Application

Figures 17A, 17B, 17C:
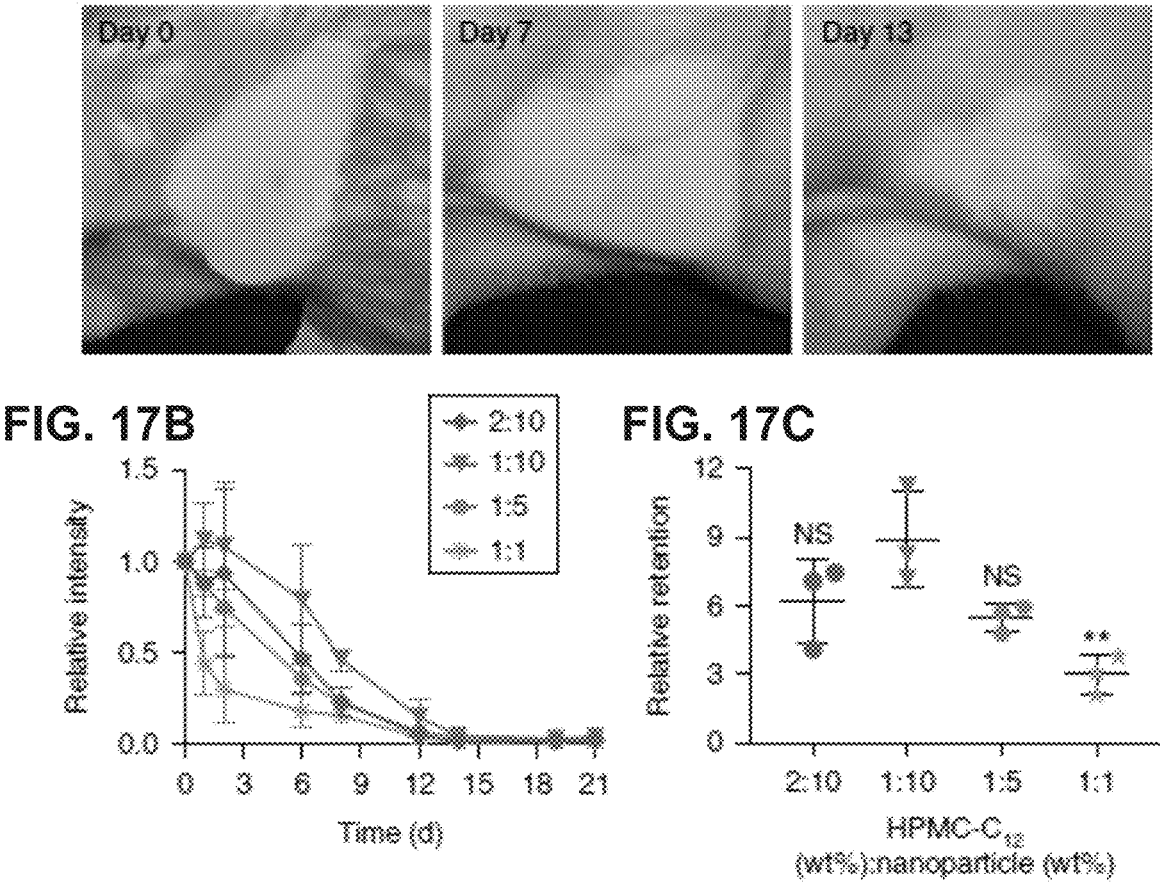
FIGS. 17A-C show in vivo retention of PNP hydrogel adhesion barrier.
Figures 18A, 18B:
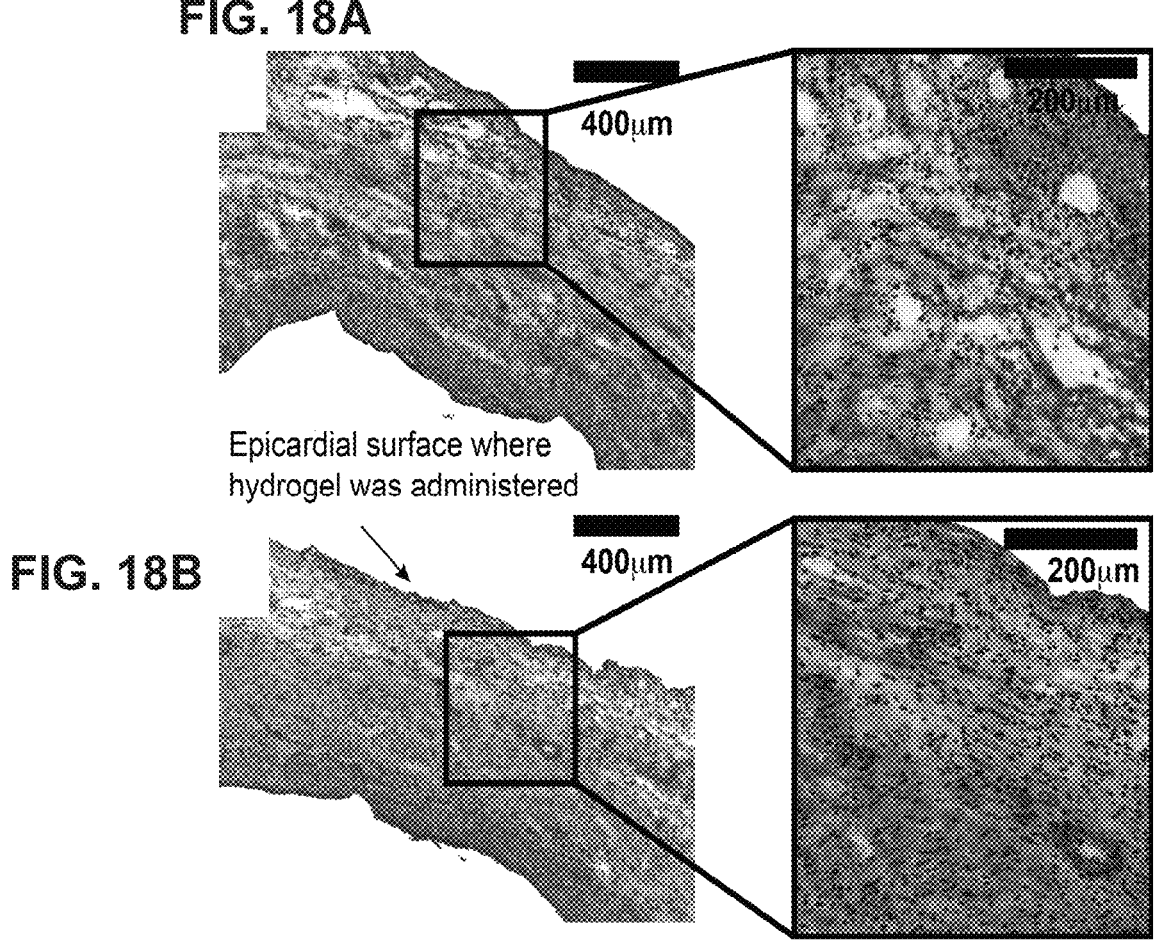
FIGS. 18A and B show experimental results re histological examination of tolerability with hematoxylin and eosin staining of PNP hydrogels.
FIG. 18B is a representative 10×H&E image of the infarct region of a PNP 1:10 hydrogel treated heart 4 weeks following myocardial infarction (left), and representative 20× image of the infarct region (right). These images demonstrate no difference in inflammatory response in hearts treated with hydrogels compared to untreated control groups.
Figure 20:
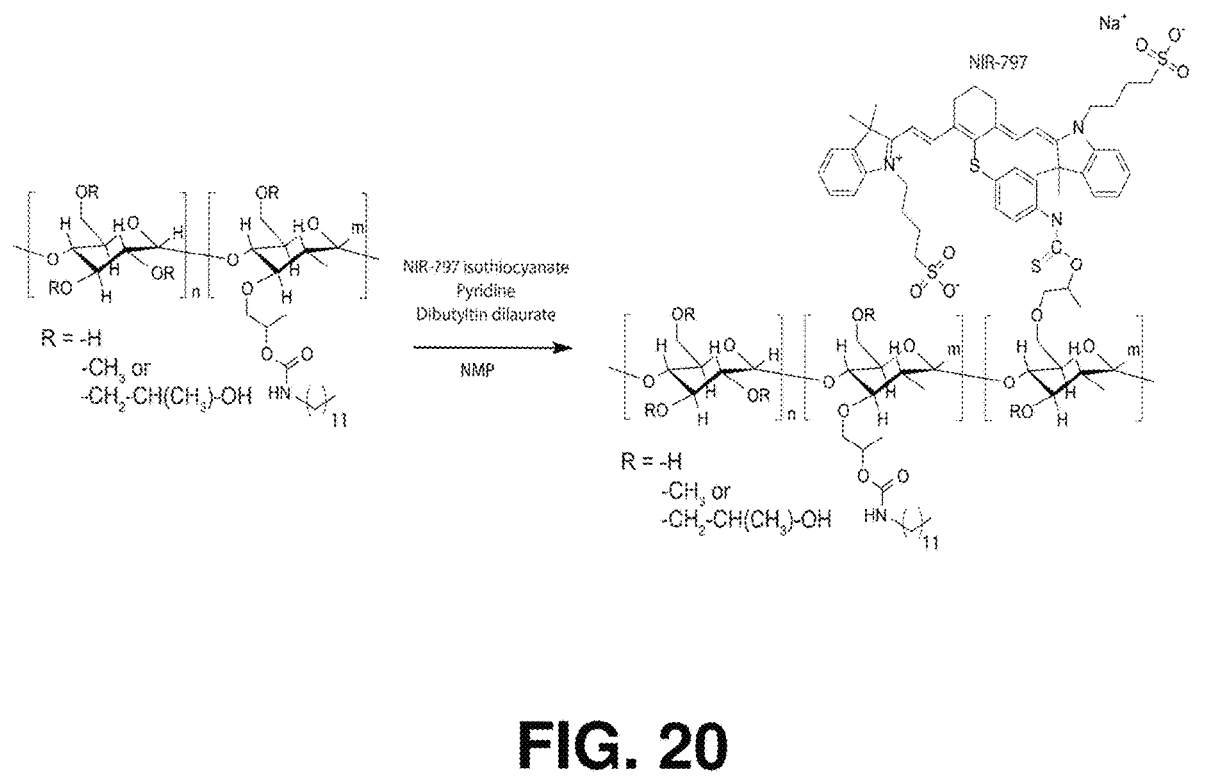

The retention timeframe of PNP 2:10, 1:10, 1:5, and 1:1 hydrogel formulations in the pericardial space following a thoracotomy was investigated with fluorescently-labeled HPMC-C$_{12}$ PNP hydrogels (FIG. 20). Near-IR light sufficiently penetrates tissue and allows for real-time imaging of the dye-labelled PNP hydrogels in the pericardial space over the 4-week cardiac adhesion formation studies. In these studies, rats were treated with NIR-797-labeled PNP hydrogel (see FIG. 20) directly following vessel occlusion and imaged on Day 0, 1, 2, 5, 7, 13, 16, 20, and 28 (FIG. 17). Following administration, hydrogels exhibited intense signal in the pericardial space at the site of application (FIG. 17A). The signal steadily declined over the course of the study, indicating that the hydrogels persisted locally in the pericardial space for approximately 2 weeks (FIG. 17B). Since the reported pathophysiology for adhesion formation occurs 7-14 days following surgery, this time frame seems to be ideal for continual coverage and adhesion prevention in the thoracic cavity. The overall relative retention for PNP 1:10 was significantly higher compared to the PNP 1:1 formulation (FIG. 17C). The increase in sustained retention in the PNP 1:10 group indicates a greater presence of material in the cardiac space over the course of the study. Due to the formulation dependency observed in the efficacy study, the overall material retention in the PNP 1:10 group seems to be beneficial for effective adhesion prevention.

Experimental Results 5—PNP Hydrogel Biocompatibility

Figures 24A, 24B, 24C, 24D, 24E, 24F, 24G, 24H, 24I:
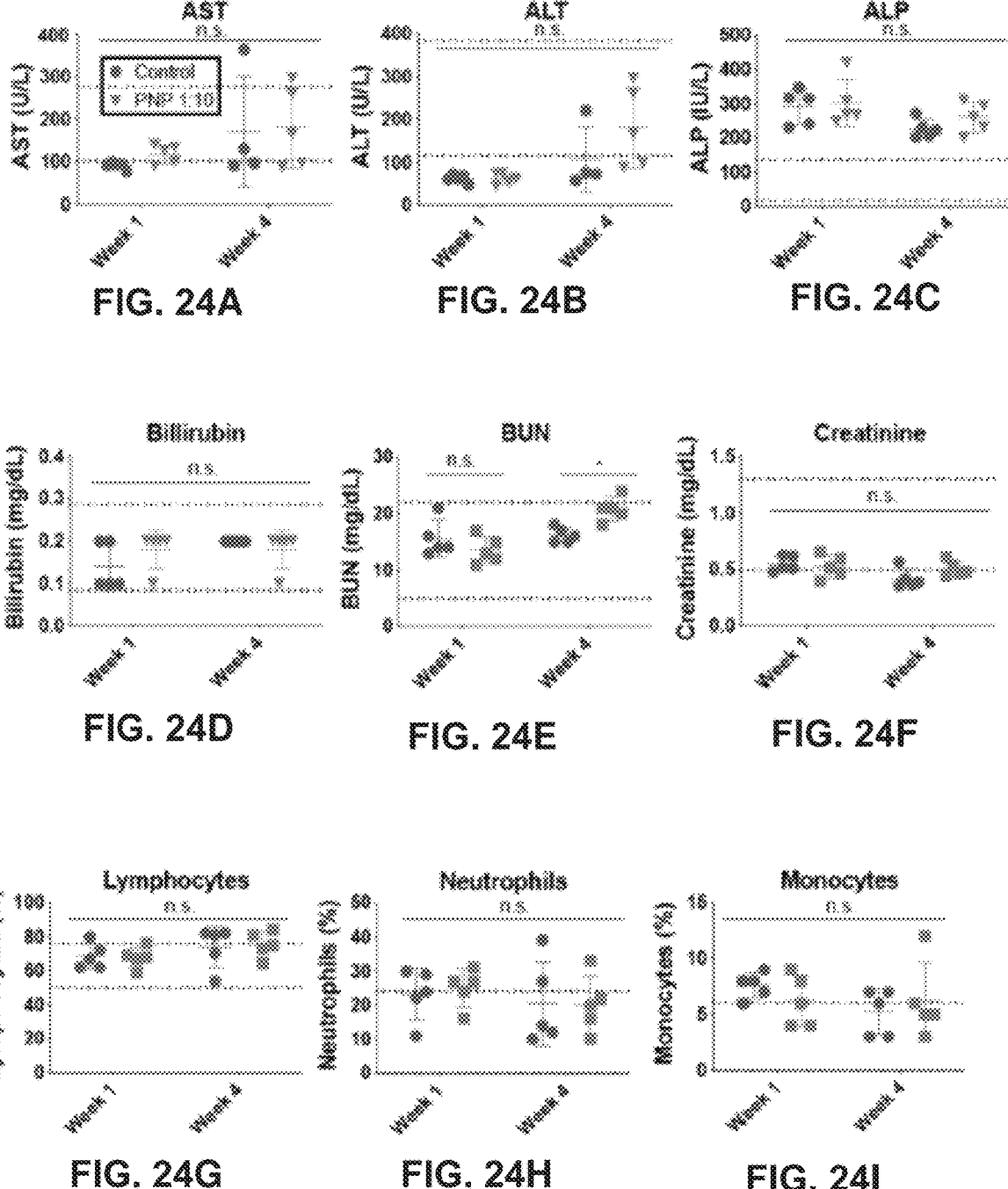
FIGS. 24A-I shows blood chemistry and complete blood counts that were performed at 1 week and 4 weeks following PNP 1:10 hydrogel administration in the thoracic cavity of rodents. The average values for the blood chemistry markers and complete blood counts remained within the normal range throughout the study period and/or resulted in no significant difference between the control group and hydrogel group. The dotted lines in each plot indicate the range of values exhibited in a healthy population of Sprague Dawley rats defined as the mean±two standard deviations. Sample size is n=5 per group. Statistical significance was determined using a two-way ANOVA (n.s=not significant).

A high degree of biocompatibility may be advantageous for effective adhesion prevention because an inflammatory response from the adhesion barrier could lead to increased adhesion formation. Accordingly, in one study, male rats underwent a sham surgery and received administration of 200 μL of PNP 1:10 hydrogel into the cardiac space or no treatment. At one week (n=5 per group) and at four weeks (n=5 per group) following surgery, rats were submitted to a pathologist and underwent complete necropsy for gross macroscopic findings. Surrounding tissues were explanted for microscopic histological analysis. A pathologist blinded to the treatment groups concluded that there were no substantial differences between the study groups. The major findings shared among both study groups included myofiber damage, fibrosis, and inflammation in the thoracic wall. These observations are attributed to the thoracotomy and not the material itself. Complete blood count and blood chemistry panels also indicated no substantial abnormalities (FIG. 24).

Figures 21A, 21B, 21C:
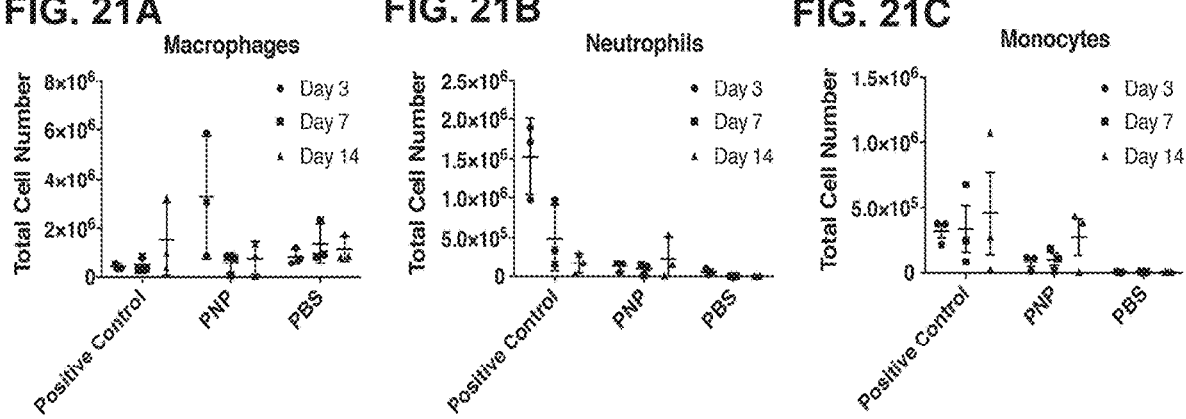
FIGS. 21A-C show flow cytometry of inflammatory cells collected from the intraperitoneal space of C57BL6 mice on Day 1, 7, and 14 following injection (200 L) of either a PNP hydrogel containing Laponite clay particles known to initiate mild inflammation (positive control), PNP 1:10 hydrogel, or PBS (negative control). CD11bmed Ly6G+ were identified as neutrophils (FIG. 21B), CD11b+ Ly6G− CD11c F4/80+ were identified as macrophages (FIG. 21A), and CD11b+ Ly6G− CD11c F4/80-Ly6C+ were identified as monocytes (FIG. 21C). PNP hydrogels demonstrate negligible inflammatory response that is comparable to PBS.

Moreover, PNP hydrogels comprising HPMC-C$_{12}$ and PEG-PLA NPs exhibit exceptional biocompatibility in mice, whereby subcutaneous and intraperitoneal implantation produces a negligible inflammatory response that is indistinguishable from that of PBS controls (see FIG. 21). The biocompatibility of the PNP hydrogels in the pericardial space of rats was investigated by explanting hearts at the end-point of the above studies for histological examination of tolerability with hematoxylin & eosin staining (FIGS. 18A and 18B). Hearts treated with PNP hydrogels were indistinguishable from that of control animals.

Experimental Results 6—Large Animal Preclinical Translation

A pilot study was conducted in a preclinical translational sheep model to further investigate the efficacy of the PNP hydrogel anti-adhesion system and address the physiologic and anatomic differences between small animals and humans related to size and inflammatory response. Instead of inducing a myocardial infarction, an epicardial abrasion model was used as a more clinically-relevant preclinical model of cardiac surgery (FIGS. 19A-E). The anterior epicardial surface of the heart was abraded using a Bovie® scratch pad for 30 seconds (FIG. 19*a*) to initiate an inflammatory response (FIG. 19B), resulting in the formation of severe adhesions. Animals (n=1 per group) were randomized to receive administration of SEPRAFILM® (12 cm$^2$), PNP 1:10 hydrogel (25 ml), or no treatment as a control. SEPRAFILM® was chosen because it is used most commonly of all the commercially-available adhesion barrier products, and the PNP 1:10 hydrogel formulation was chosen because it exhibited the lowest adhesion score in the rodent model.

Figures 25A, 25B, 25C:
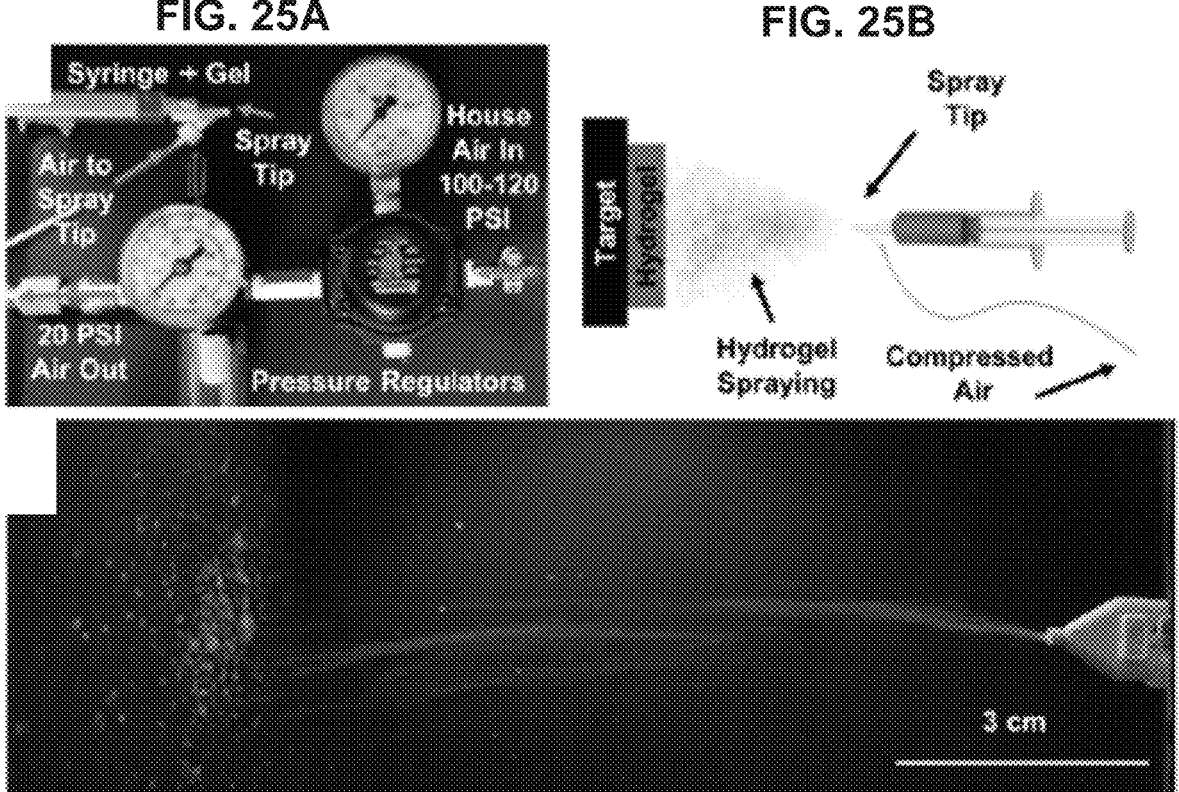
FIG. 25A shows an image of a prototype hydrogel sprayer system.
FIG. 25B is a schematic representation of the hydrogel being sprayed from a syringe using compressed air.
FIG. 25C is a screen capture from a video of the PNP 1:10 hydrogel formulation being sprayed and adhering to a target.

PNP hydrogels were sprayed onto the epicardial surface of the heart, which allowed for uniform coverage of the epicardial tissue. The PNP hydrogels could be easily sprayed using compressed air and a spray nozzle (FIGS. 19C and 19*f*; FIG. 25). Hydrogel application was completed in under 2 min. A 30 mL syringe was loaded with PNP hydrogel (25 mL) and attached to a TISSEEL® spray nozzle along with a compressed air line to provide the pressure necessary to spray the hydrogel onto the tissue. After the epicardial surface was completely coated with PNP 1:10 hydrogel (25 mL; FIG. 19G), the thoracotomy was closed. SEPRAFILM® was applied according to the manufacturer's specifications.

After 4 weeks, animals underwent a sternotomy, the pericardial adhesions were released using blunt and/or sharp dissection as necessary, and the heart was dissected until all the major epicardial structures were exposed, including the left and right atrial appendage, left and right ventricle, LAD, main pulmonary artery, ascending aorta and the superior and inferior vena cavae. During this process, the surgeon assessed the severity of adhesions using the same double-blinded clinical-scoring system described in the rat study above. The region of interest for adhesion assessment was the anterior surface of the heart where the abrasion occurred. On completion of heart dissection, an image was captured and the heart was explanted. FIG. 19H is a representative image of a human heart during redo surgery before heart dissection. This picture is provided to demonstrate the severity of adhesions observed in the clinical setting, which the model described herein attempts to emulate. When comparing FIG. 19H with FIG. 19I, which shows an untreated sheep heart before dissection, there are severe adhesions present in both, demonstrating the ability of the abrasion model to generate robust adhesions. FIG. 19J shows an attempt to release pericardial adhesions from untreated and SEPRAFILM®-treated hearts during the heart-dissection process. Pericardial adhesions were tightly adhered to the epicardial surface and could not be completely removed without excessive risk of damaging the heart. FIG. 19K (untreated) and FIG. 19M (SEPRAFILM®) show a substantial amount of tissue remaining on the epicardial surface as a result of tight adhesions. As a result of the pericardial adhesions, the untreated (FIG. 19K) and SEPRAFILM®-treated (FIG. 19M) hearts closely resembled the human heart during a redo surgery and received severe adhesion scores of 4 and 5, respectively. By contrast, the PNP 1:10-treated heart appeared markedly different from those of the control and SEPRAFILM®-treated groups and received an adhesion severity score of 0. Indeed, the pericardium could be lifted directly off the hydrogel-treated heart (FIG. 19N), revealing a pristine epicardial surface below (FIG. 19O). The dissection of the PNP hydrogel-treated heart was easier compared to that required for the control and SEPRAFILM®-treated hearts, as all the major cardiac structures were completely and immediately visible after lifting the pericardium off the heart. FIG. 19O shows the successful and complete removal of tissue surrounding the heart treated with PNP 1:10.

Experimental Results 7—Cardiopulmonary Bypass and Aortotomy Model

Figures 22A, 22B, 22C, 22D, 22E, 22F, 22G, 22H:
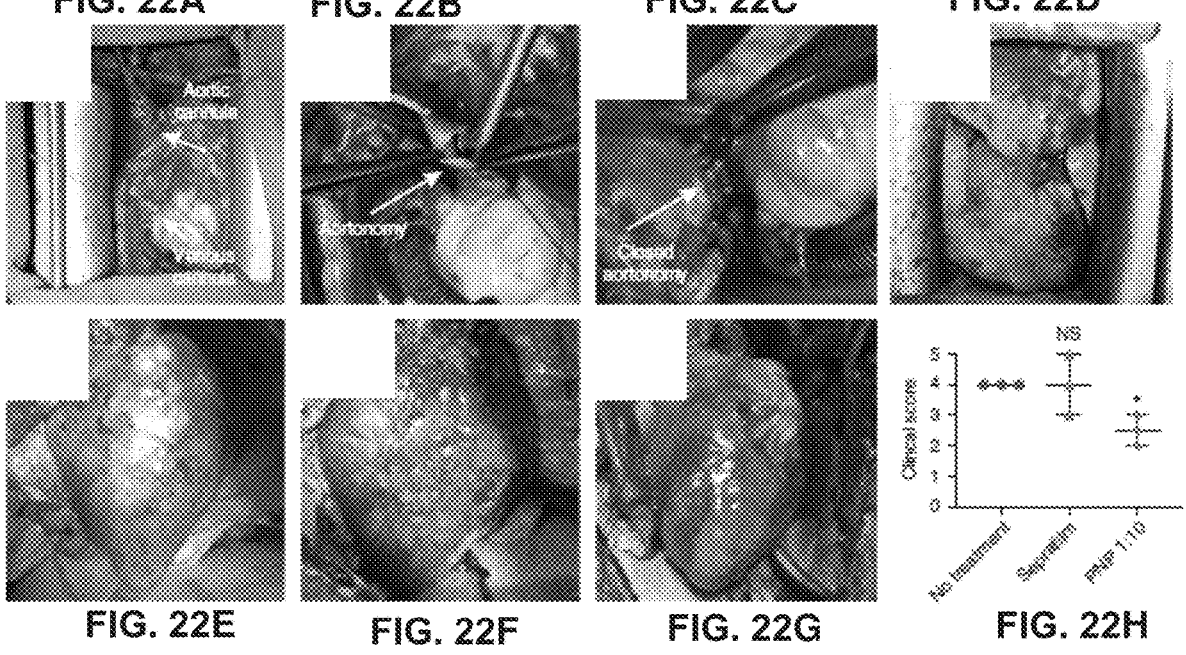
FIGS. 22A-H show a sheep cardiopulmonary bypass and aortotomy model.
Figure 26:
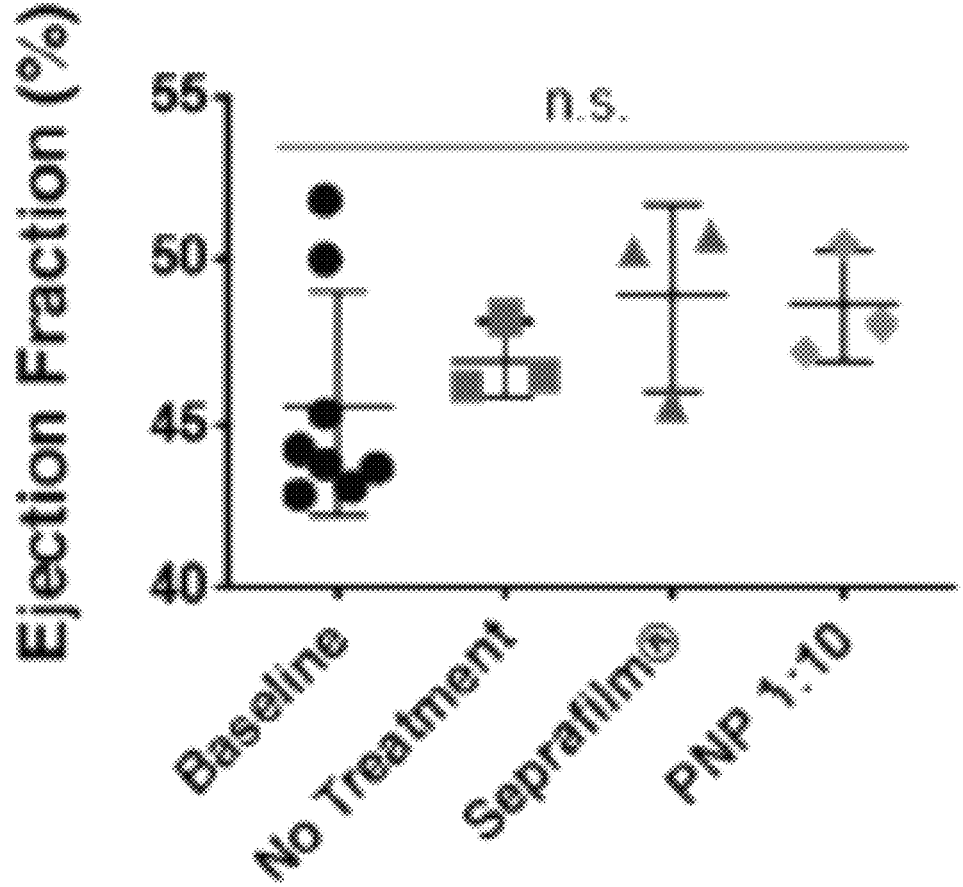
FIG. 26 shows ejection fraction data from cardiac MRI performed 4 weeks following cardiopulmonary bypass. Baseline measurements represent healthy sheep prior to the cardiopulmonary bypass procedure. There is no statistical difference between treatments groups and the baseline 4 weeks following the procedure.

The efficacy of the PNP hydrogel anti-adhesion system using a clinically relevant cardiopulmonary bypass and aortotomy model was also performed. Using central cannulation of the aortic arch and right atrium (FIG. 22A) and a pulmonary artery venting catheter to decompress the left ventricle, a 2 cm partial transverse aortotomy was performed on an arrested heart on cardiopulmonary bypass. The aortic valve was inspected to mimic a standard aortic valve surgery (FIG. 22B). The aortotomy was closed, the heart was reperfused and deaired, cardiopulmonary bypass was weaned off (FIG. 22C) and all cannulas were removed. Hemostasis was ensured at all surgical sites. At this point, sheep (n=3 per group) were randomized to receive SEPRAFILM® (24 cm²), PNP 1:10 hydrogel (50 ml) or no treatment. Similar to the epicardial abrasion model described above, PNP hydrogels were sprayed using compressed air and a spray nozzle (FIG. 22C,F) on the surface of the heart, including all surgical sites. After the heart surface was completely and uniformly coated with PNP 1:10 hydrogel (50 ml; FIG. 22D), the thoracotomy was closed. SEPRAFILM® was applied as a sheet over the surface of the heart, including all surgical sites. Sheep underwent baseline and four-week magnetic resonance imaging to assess heart function and ensure consistency across treatment groups (FIG. 26).

Figures 27A, 27B, 27C, 27D, 27E, 27F, 27G, 27H, 27I:
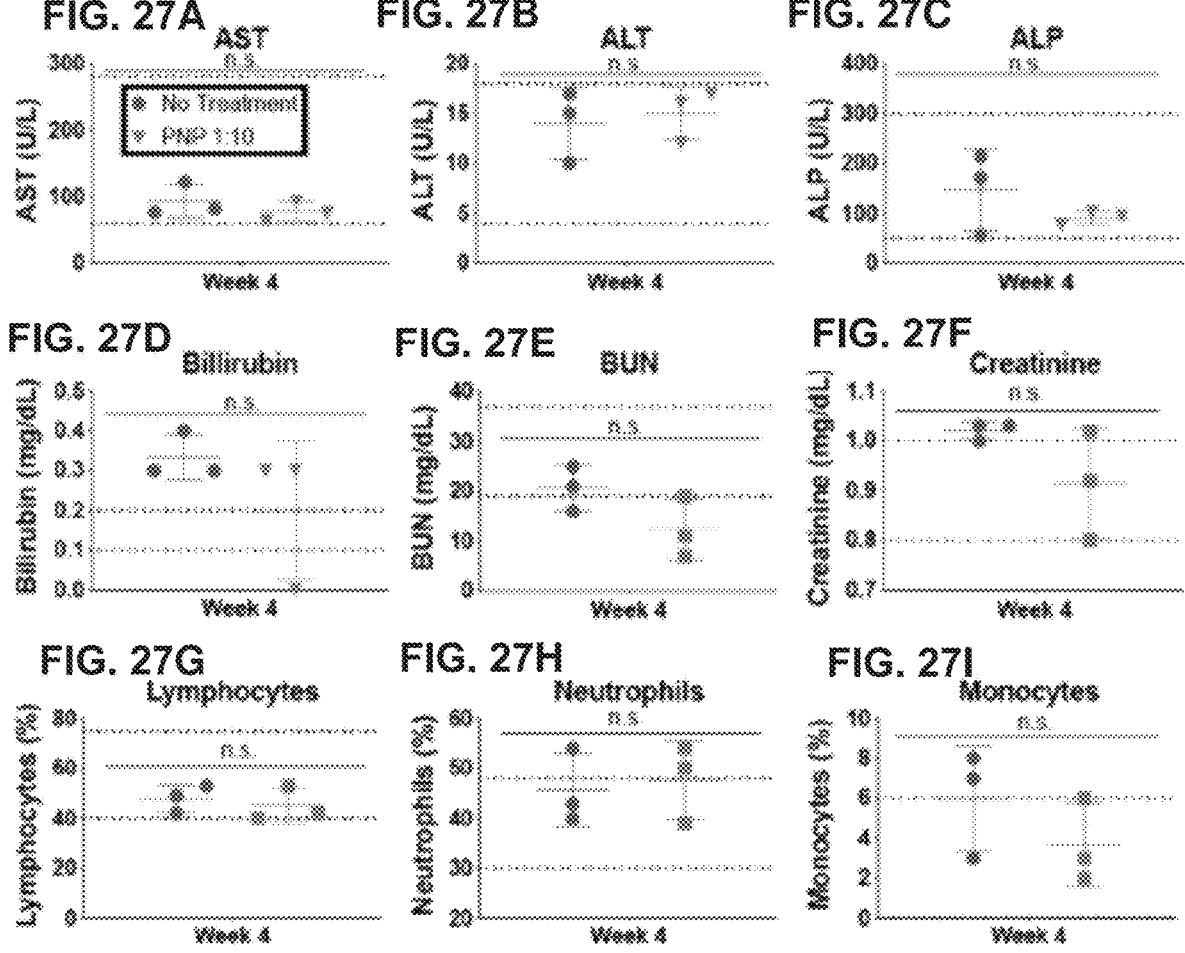
FIGS. 27A-I show blood chemistry and complete blood counts that were performed 4 weeks following the ovine cardiopulmonary bypass procedure. The average values for the blood chemistry markers and complete blood counts remained within the normal range throughout the study period and/or resulted in no significant difference between the control group and hydrogel group. The dotted lines in each plot indicate the range of values exhibited in a healthy population of Dorsett sheep defined as the mean±two standard deviations. Sample size is n=3 per group. Statistical significance was determined using a two-way ANOVA (n.s=not significant).

After four weeks, sheep underwent median sternotomy and the pericardial adhesions were released. Again, the heart was dissected until all the major cardiac structures were exposed, including all surgical and cannulation sites. During this process, the surgeon assessed the severity of adhesions using the same double-blinded clinical-scoring system described in the rat study and sheep epicardial abrasion study above. The region of interest for the adhesion assessment was the epicardial surface of the heart. On completion of heart dissection, an image was captured, the heart was explanted and the adhesion severity was scored. FIG. 22E (untreated) and FIG. 22F (SEPRAFILM®) show tissue remaining on the heart surface as a result of severe adhesion formation. Consequently, the untreated (FIG. 22E) and SEPRAFILM®-treated (FIG. 22F) hearts received poor adhesion scores of 4±0 and 4±1, respectively. By contrast, the PNP 1:10-treated heart (FIG. 22G) resulted in much easier dissection, less severe adhesion formation and identifiable coronary vessels, resulting in a score of 2.5±0.5 (P<0.05; FIG. 22H). Complete blood count and blood chemistry panels, conducted at four weeks, indicated no significant abnormalities between groups (FIG. 27).

CONCLUSION

The experimental results described herein demonstrate that a supramolecular polymeric hydrogel (e.g., a PNP hydrogel) with complex viscoelastic and flow properties as described herein can effectively prevent the formation of post-operative cardiac adhesions. For example, the experimental results described herein show that the viscoelastic adhesion barrier can allow the pericardium to be lifted off the heart 4 weeks after initial surgery, revealing a clear epicardial surface below (i.e., where the gel is no longer present and there are no adhesions).

The biodegradable, shear-thinning and viscoelastic PNP hydrogels described herein are advantageously easy and inexpensive to manufacture on scale, are exceedingly easy to use, and are highly effective in prevention of adhesions. Further, the PNP hydrogel barrier described herein can thus rely on complex viscoelastic behavior to maintain natural movement between tissues and organs.

The anti-adhesion PNP hydrogel described herein can be configured to achieve viscous flow when shear is applied (e.g., spraying), allowing it to conform to and completely cover the target tissue. After the hydrogel is applied, it can rapidly take form of a solid-like physical barrier that adheres to the tissue, does not delaminate, and remains solid in the relatively low perturbed environment near the heart. The hydrogel can further be configured to allow flow between neighboring body structures while remaining adhered to the tissue allowing it to adjust to natural movement within the body. PNP hydrogels demonstrate this behavior as yield stress fluids that are solid-like (G'>G") below certain strains/stresses (FIG. 15E), but flow like viscous fluids above a critical stress/strain value, as shown in FIG. 15F. In addition, PNP hydrogels self-heal rapidly to reversibly transition from viscous flow back into a solid like barrier, allowing the hydrogels to quickly adhere and settle onto the target tissue.

It is the distinct mechanical properties of the adhesion barrier described herein that dictate its efficacy. Based upon the experiments described herein, there are some key design parameters that appear to be helpful for a successful adhesion barrier. In some embodiments, the physical characteristics of the PNP hydrogel that provide the adhesion prevention as desired and described herein include:

1. A storage modulus (G') of 10-1000 Pa, such as 50-500 Pa, such as 100-200 Pa. The storage modulus can, for example, be observed at a frequency of 10 rad/s and at a strain within the linear viscoelastic regime of the material using an oscillatory shear test in a parallel plate rheometer.

2. A yield stress of 1-1000 Pa, such as 50-500 Pa, such as 100-200 Pa. The yield stress can, for example, be observed using a stress ramp in a parallel plate rheometer.

3. A linear viscoelasticity (defined as range of strains where tan delta (G"/G') is strain-independent) maintained at strains up to at least 0.5%, such as at least 5%, such as at least 50%. The linear viscoelasticity can, for example, be observed in an oscillatory strain amplitude sweep observed at a frequency of 10 rad/s in a parallel plate rheometer, where about 1% is preferred.

4. A tan delta (defined as the ratio of the loss modulus over the storage modulus (G"/G')), of less than 1, such as between 0.3-0.5. The tan delta can, for example, be observed in an oscillatory shear test at a frequency of 10 rad/s and a strain within the linear viscoelastic regime of the material using a parallel plate rheometer.

The variation in clinical score between the PNP hydrogels of the experimental results described herein demonstrate how modulus/viscoelasticity and the yield stress can be useful for determining the effectiveness of the material as an adhesion barrier. Liquid-like formulations with their high tan δ at low strains and frequencies may perform poorly because they never form a solid-like barrier. Solid-like formulations show a correlation between the yield stress and storage modulus to the effectiveness as an adhesion barrier. The PNP 1:10 hydrogel formulation had the lowest adhesion score compared to the other gel formulations with an intermediate storage modulus and yield stress. Materials that are too soft and/or weak may flow too easily when perturbed in the body and leave the target tissue area too quickly while adhesions are still developing. Materials that are too stiff and/or strong may be more difficult to deposit, easily detach from the tissue if the yield stress is higher than the adhesion strength, and be more difficult to spread uniformly over a target area. Cohesive failure, which occurs when the yield stress is lower than the adhesion strength, allows the gel to be smeared or spread on the surface without delaminating, resulting in a barrier capable of being agitated without being removed from the tissue surface. This rationale is consistent with the variability observed in the adhesion score of PNP 2:10 hydrogel, where the increased yield strength may have prevented cohesive failure and led to more detachments of the gel from target tissues over the 4 week study period.

This anti-adhesion PNP hydrogel provides easy and scalable synthesis. Further, the anti-adhesion PNP hydrogel system described herein can be used in a variety of surgeries and can produce a dramatic reduction in both incidence and severity of adhesions.

In some embodiments, the anti-adhesion PNP hydrogel can be applied in multiple-stage surgeries (e.g., heart repairs) to prevent adhesion between the stages and therefore reduce the time required for surgery (e.g., reduce or eliminate the time required to remove adhesions). For example, the second-stage surgery can take less than 30 minutes.

In some embodiments, the anti-adhesion PNP hydrogel can be placed applied tissue layers for adhesion prevention. For example, the PNP hydrogel can be applied between a tendon and sheath (e.g., during hand surgery) to prevent adhesion of the sheath to the tendon after surgery (and to therefore allow for free sliding of the tendon relative to the sheath).

In some embodiments, the PNP hydrogel can allow for translational use in laparoscopic surgeries.

The PNP hydrogel described herein can advantageously be formed and engineered to optimize the physical characteristics, as outlined herein (e.g., shear-thinning, viscoelasticity, and rapid self-healing), for maintaining separation between tissues and organs, thus preventing adhesion formation.

The PNP hydrogel described herein can include additionally or alternatively include any of the characteristics and/or features of the hydrogels described in U.S. Publication No. 2017/0319506, the entirety of which is incorporated by reference herein.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached, or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A method comprising:
applying a supramolecular hydrogel to a tissue after a surgical procedure performed on or proximate to the tissue, the supramolecular hydrogel comprising a hydrophobically modified cellulose derivative non-covalently cross-linked with a plurality of nanoparticles; and
inhibiting formation of an adhesion on the tissue with the applied supramolecular hydrogel.

2. The method of claim 1, wherein the supramolecular hydrogel comprises from 5 wt % to 10 wt % of the nanoparticles.

3. The method of claim 1, wherein the nanoparticles comprise poly(ethylene glycol)-block-poly(lactic acid) (PEG-PLA).

4. The method of claim 1, wherein the supramolecular hydrogel comprises from 1 wt % to 2 wt % of the hydrophobically modified cellulose derivative.

5. The method of claim 1, wherein the hydrophobically modified cellulose derivative comprises one or more of hydroxypropylmethylcellulose (HPMC), hydroxyethyl cellulose (HEC), hydroxypropylcellulose (HPC), ethylcellulose (EC), methylcellulose (MC), hydroxyethylmethylcellulose (HEMC), carboxymethylcellulose (CMC), or carboxymethyl ethyl cellulose (CMEC).

6. The method of claim 1, wherein the hydrophobically modified cellulose derivative is a cellulose derivative modified with a hydrophobic saturated alkyl moiety, a hydrophobic unsaturated alkyl moiety, or a hydrophobic aryl moiety.

7. The method of claim 1, wherein the supramolecular hydrogel is shear-thinning.

8. The method of claim 1, wherein the supramolecular hydrogel is self-healing.

9. The method of claim 1, wherein the supramolecular hydrogel is applied by injecting, spreading, or spraying.

10. The method of claim 1, wherein the tissue comprises one or more of abdominal tissue, orthopedic tissue, thoracic tissue, cardiac tissue, or gynecologic tissue.

11. A method comprising:
administering a dynamically cross-linked hydrogel to a tissue after a surgical procedure performed on or proximate to the tissue to inhibit adhesion formation, the dynamically cross-linked hydrogel comprising non-covalent interactions between a hydrophobically modified cellulose derivative and a plurality of nanoparticles.

12. The method of claim 11, wherein the dynamically cross-linked hydrogel comprises from 5 wt % to 10 wt % of the nanoparticles.

13. The method of claim 11, wherein the nanoparticles comprise poly(ethylene glycol)-block-poly(lactic acid) (PEG-PLA).

14. The method of claim 11, wherein the dynamically cross-linked hydrogel comprises from 1 wt % to 2 wt % of the hydrophobically modified cellulose derivative.

15. The method of claim 11, wherein the hydrophobically modified cellulose derivative comprises one or more of hydroxypropylmethylcellulose (HPMC), hydroxyethyl cellulose (HEC), hydroxypropylcellulose (HPC), ethylcellulose (EC), methylcellulose (MC), hydroxyethylmethylcellulose (HEMC), carboxymethylcellulose (CMC), or carboxymethyl ethyl cellulose (CMEC).

16. The method of claim 11, wherein the hydrophobically modified cellulose derivative is a cellulose derivative modified with a hydrophobic saturated alkyl moiety, a hydrophobic unsaturated alkyl moiety, or a hydrophobic aryl moiety.

17. The method of claim 11, wherein the dynamically cross-linked hydrogel is shear-thinning.

18. The method of claim 11, wherein the dynamically cross-linked hydrogel is self-healing.

19. The method of claim 11, wherein the dynamically cross-linked hydrogel is administered by injecting, spreading, or spraying.

20. The method of claim 11, wherein the tissue comprises one or more of abdominal tissue, orthopedic tissue, thoracic tissue, cardiac tissue, or gynecologic tissue.

* * * * *